(12) United States Patent
Greenberg et al.

(10) Patent No.: US 8,060,216 B2
(45) Date of Patent: Nov. 15, 2011

(54) METHOD AND APPARATUS TO PROVIDE SAFETY CHECKS FOR NEURAL STIMULATION

(75) Inventors: Robert Jay Greenberg, Los Angeles, CA (US); Kelly Hobart McClure, Simi Valley, CA (US); James Singleton Little, Saugus, CA (US); Rongqing Dai, Valencia, CA (US); Arup Roy, Santa Clarita, CA (US); Richard Agustin Castro, Pasadena, CA (US); John Reinhold, Tarzana, CA (US); Kea-Tiong Tang, Temple City, CA (US); Sumit Yadav, Los Angeles, CA (US); Chunhong Zhou, Pasadena, CA (US); Dao Min Zhou, Saugus, CA (US); Pishoy Maksy, Sherman Oaks, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 957 days.

(21) Appl. No.: 11/796,433

(22) Filed: Apr. 27, 2007

(65) Prior Publication Data
US 2007/0265686 A1 Nov. 15, 2007

Related U.S. Application Data

(63) Continuation-in-part of application No. 11/413,771, filed on Apr. 28, 2006.

(51) Int. Cl.
*A61N 1/18* (2006.01)
(52) U.S. Cl. .............. 607/63; 607/45; 607/118
(58) Field of Classification Search .......... 607/45, 607/46, 118, 72, 63
See application file for complete search history.

(56) References Cited

U.S. PATENT DOCUMENTS

| | | | |
|---|---|---|---|
| 5,109,844 A | 5/1992 | de Juan, Jr. et al. | |
| 5,507,785 A * | 4/1996 | Deno | 607/24 |
| 5,755,744 A * | 5/1998 | Shaw et al. | 607/45 |
| 5,935,155 A | 8/1999 | Humayun et al. | |
| 5,944,747 A | 8/1999 | Greenberg et al. | |
| 6,718,209 B2 | 4/2004 | Williamson et al. | |
| 6,974,533 B2 | 12/2005 | Zhou | |
| 7,065,403 B1 * | 6/2006 | Mouchawar et al. | 607/8 |
| 2005/0222624 A1 | 10/2005 | Greenberg et al. | |

* cited by examiner

*Primary Examiner* — Carl H Layno
*Assistant Examiner* — Pamela M Bays
(74) *Attorney, Agent, or Firm* — Scott B. Dunbar; Tomas Lendvai

(57) ABSTRACT

Electronic neural tissue stimulators for controlling the level of electrical stimulation in order to prevent damage to the neural tissue. Methods presented in the disclosure include detecting current leakage via electrode impedance measurement, electrode capacitance measurement, and testing the electrode response to a test current pulse. Apparatus presented in the disclosure include circuitry and systems capable of performing the methods disclosed.

6 Claims, 16 Drawing Sheets

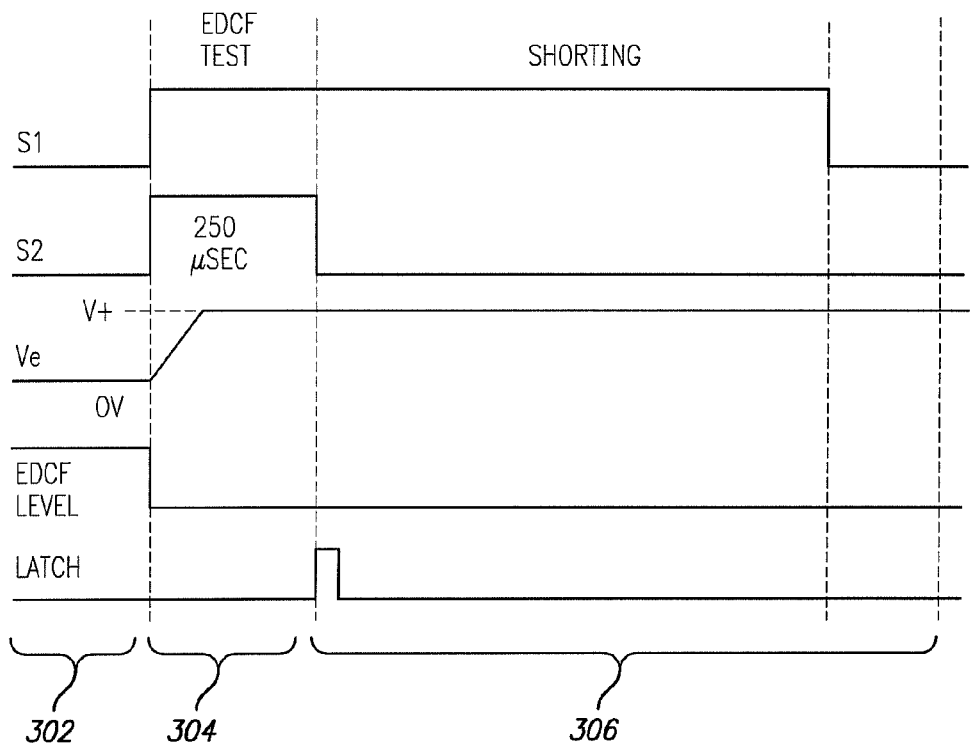
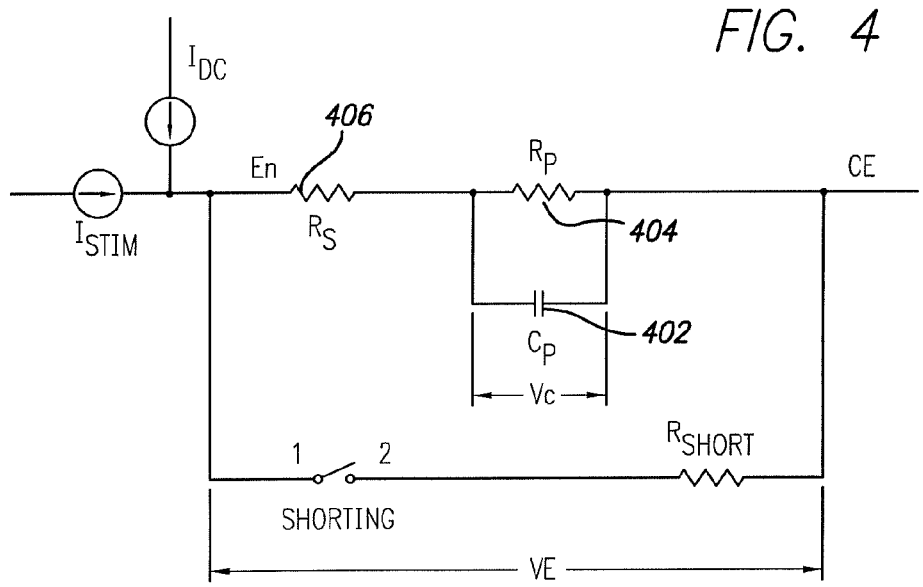

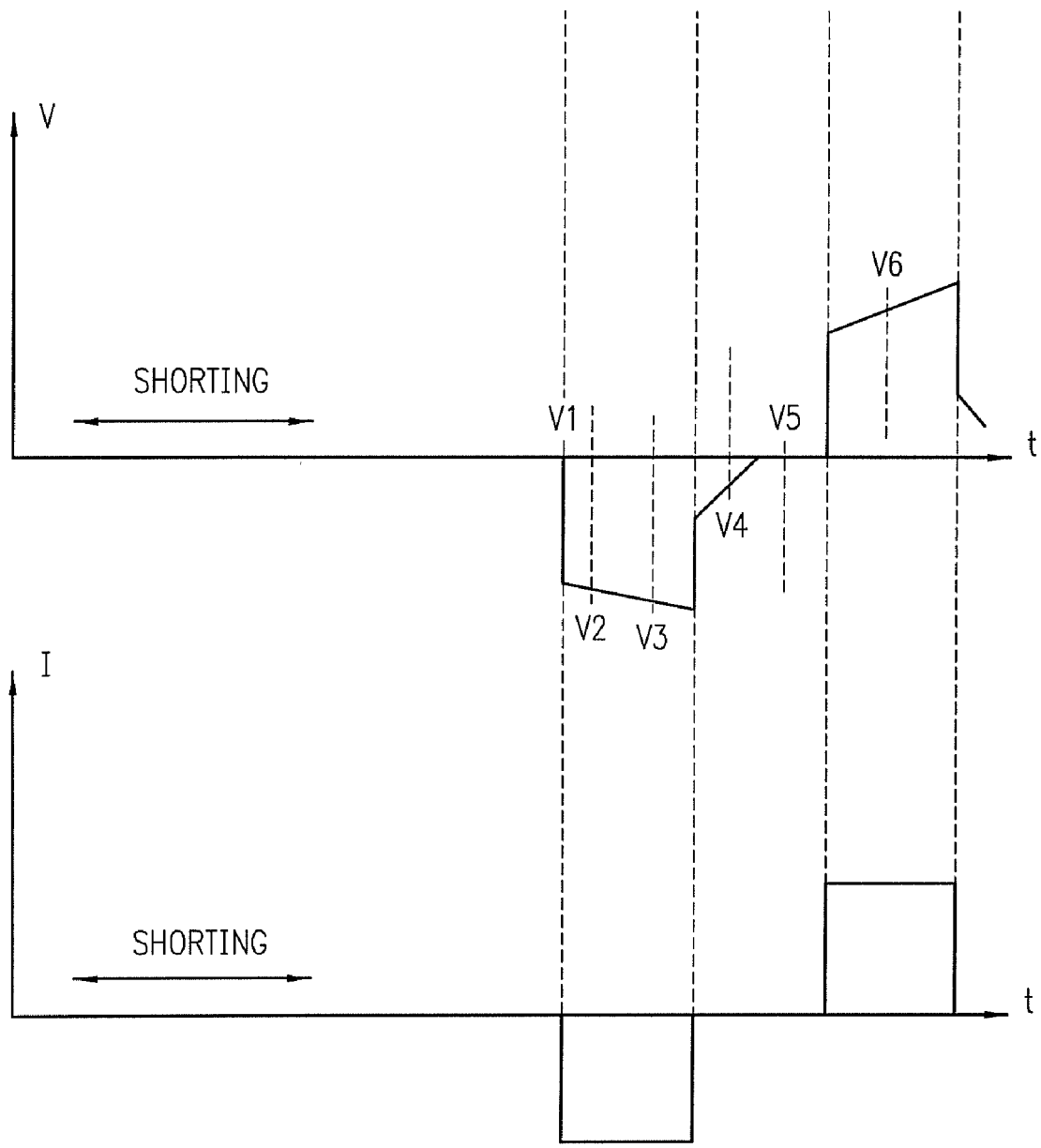

METHOD AND APPARATUS TO PROVIDE SAFETY CHECKS FOR NEURAL STIMULATION

CROSS REFERENCE TO RELATED APPLICATIONS

This application is a continuation-in-part of, and claims the benefit of, U.S. non-provisional patent application Ser. No. 11/413,771 filed on Apr. 28, 2006, for "Method and Apparatus to Provide Safety Checks for Neural Stimulation" by Robert Greenberg, M.D. PhD, et al., the disclosure of all of which is incorporated herein by reference.

FEDERALLY SPONSORED RESEARCH OR DEVELOPMENT

The present invention was made with support from the United States Government under Grant No. R24EY12893-01, awarded by the National Institutes of Health. The government has certain rights in the patent.

FIELD

The present disclosure is generally directed to neural stimulation and, more specifically, to an improved method of providing safety checks to prevent neural damage.

BACKGROUND

In 1755, LeRoy passed the discharge of a Leyden jar through the orbit of a man who was blind from cataract and the patient saw "flames passing rapidly downwards." Ever since, there has been a fascination with electrically elicited visual perception. The general concept of electrical stimulation of retinal cells to produce these flashes of light or phosphenes has been known for quite some time. Based on these general principles, some early attempts at devising prosthesis for aiding the visually impaired have included attaching electrodes to the head or eyelids of patients. While some of these early attempts met with some limited success, these early prosthetic devices were large, bulky and could not produce adequate simulated vision to truly aid the visually impaired.

In the early 1930's, Foerster investigated the effect of electrically stimulating the exposed occipital pole of one cerebral hemisphere. He found that, when a point at the extreme occipital pole was stimulated, the patient perceived a small spot of light directly in front and motionless (a phosphene). Subsequently, Brindley and Lewin (1968) thoroughly studied electrical stimulation of the human occipital (visual) cortex. By varying the stimulation parameters, these investigators described in detail the location of the phosphenes produced relative to the specific region of the occipital cortex stimulated. These experiments demonstrated: (1) the consistent shape and position of phosphenes; (2) that increased stimulation pulse duration made phosphenes brighter; and (3) that there was no detectable interaction between neighboring electrodes which were as close as 2.4 mm apart.

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

In 1975, Dawson and Radtke stimulated a cat's retina by direct electrical stimulation of the retinal ganglion cell layer. See Investigative Ophthalmology & Visual Science Reports, vol. 16, no. 3, p. 249 (1977). These experimenters placed nine and then fourteen electrodes upon the inner retinal layer (i.e., primarily the ganglion cell layer) of two cats. Their experiments suggested that electrical stimulation of the retina with 30 to 100 µA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to at least one electrode positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., E. de Juan, et al., 99 Am. J. Ophthalmol. 272 (1985). These retinal tacks have proved to be biocompatible and remain embedded in the retina, and choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

SUMMARY

In electrically stimulating neural tissue it is usually important to prevent over stimulation and unbalanced stimulation which would cause damage to the neural tissue, the electrode, or both. It is typically critical that neural tissue in not subjected to any direct current or alternating current above a safe threshold. Further, it is usually important to identify defective electrodes as continued use may result in neural and further electrode damage. The present disclosure presents system and stimulator control mechanisms to prevent damage to neural tissue.

According to a first aspect, a method of controlling the stimulation of neural tissue is disclosed, comprising: providing a neural stimulator including at least one electrode suitable to stimulate neural tissue; testing the impedance of the at least one electrodes; calculating an average impedance; calculating a difference from said average impedance for each said at least one electrode; and determining bad electrodes based on said difference and a predetermined value.

According to a second aspect, a method of controlling the stimulation of neural tissue is disclosed, comprising: providing a neural stimulator including at least one electrode suitable to stimulate neural tissue; determining a safe level for the at least one electrode; receiving input for neural stimulation; calculating a sum of stimulation on the at least one electrode based on said input for neural stimulation; reducing the stimulation on each said at least one electrode by the amount necessary not to exceed said safe level for the at least one electrode; and stimulating said neural tissue according to a reduced stimulation level.

According to a third aspect, a method of controlling the stimulation of neural tissue is disclosed, comprising: providing a neural stimulator including at least one electrode suitable to stimulate neural tissue; receiving input for neural stimulation; determining a desired cathodic pulse based on said input; calculating a anodic pulse to balance said cathodic pulse; and stimulating neural tissue according to said cathodic and anodic pulses.

According to a fourth aspect, a neural stimulator is provided, comprising: a neural stimulation controller; at least one electrode suitable to stimulate neural tissue and driven by said neural stimulation controller; an impedance meter for measuring the impedance of the at least one electrode; a calculating device for calculating the average impedance of the at least one electrode; a calculating device for calculating the impedance difference from said average impedance for each said at least one electrode; and a means for determining bad electrodes based on said difference and a predetermined value.

According to a fifth aspect, a neural stimulator is provided, comprising a neural stimulation controller; at least one driver controlled by said neural stimulation controller; at least one electrode suitable to stimulate neural tissue driven by said at least one driver; at least one switch connecting the output of said at least one driver to a common line; and a comparator comparing voltage on said common line to a predetermined reference voltage.

According to a sixth aspect, a method of controlling the stimulation of neural tissue is disclosed, comprising: providing a neural stimulator and at least one electrode suitable to stimulate neural tissue; testing the capacitance of the at least one electrode; recording changes in capacitance over time; and determining bad electrodes based on said change in capacitance.

According to a seventh aspect, a method of controlling the stimulation of neural tissue is disclosed, comprising: providing a neural stimulator including at least one electrode suitable to stimulate neural tissue; determining a maximum charge per phase for the at least one electrode; receiving input for neural stimulation; calculating a discrete integral of the wave form of the input; reducing the stimulation on each said at least one electrode by the amount necessary not to exceed said safe level for the at least one electrode; and stimulating said neural tissue according to a reduced stimulation level.

According to an eighth aspect, a method of controlling the stimulation of neural tissue is disclosed, comprising: providing a neural stimulator including at least one electrode suitable to stimulate neural tissue; stimulating neural tissue in accordance with external input; testing total power dissipation of said neural stimulator; comparing said total power dissipation to a predetermined maximum power dissipation; and reducing stimulation if the total power dissipation exceeds said predetermined maximum power dissipation.

According to a ninth aspect, a method of controlling the stimulation of neural tissue is disclosed, comprising: providing a neural stimulator including at least one stimulating electrode and one common electrode, suitable to stimulate neural tissue; stimulating neural tissue in accordance with external input using balanced biphasic pulses in opposite phases at the same time across said at least one stimulating electrode; and disallowing stimulation waveforms on said at least one electrode that overlap non-contiguously during opposite phases with other said electrodes in the array in a bipolar or multipolar configuration.

According to a tenth aspect, a method of controlling the stimulation of neural tissue is disclosed, comprising: providing a neural stimulator including at least one electrode suitable to stimulate neural tissue; measuring electrode impedance using driver output voltage; stimulating neural tissue according to external input; measuring an after stimulation driver output voltage; and calculating leakage current using electrode impedance and after stimulation driver output voltage.

According to an eleventh aspect, an apparatus for controlling the stimulation of neural tissue is provided, comprising: a neural stimulator; at least one electrode suitable to stimulate neural tissue; a meter device for testing the impedance of the at least one electrode; a calculating device for calculating an average impedance; a calculating device for calculating a difference from said average impedance for each electrode.

According to a twelfth aspect, an apparatus for controlling the stimulation of neural tissue is provided, comprising: a neural stimulator; at least one electrode suitable to stimulate neural tissue; a meter device for testing the capacitance of the at least one electrode; a data storage device for recording changes in capacitance over time.

According to a thirteenth aspect, a neural stimulator is provided, comprising: a neural stimulation controller capable of providing a biphasic current pulse to each the electrodes; at least one electrode suitable to stimulate neural tissue driven by said neural stimulation controller; a meter device for taking at least one measurement of an IR drop of the at least one electrode when subjected to the biphasic current pulse; a calculating device for calculating a resistance for each of the at least one electrode; a calculating device for calculating a threshold leakage voltage value for each of the at least one electrode; and a data storage device for logging failed electrodes based on at least the IR drop measurement and the threshold leakage voltage values.

According to a fourteenth aspect, a method of controlling the stimulation of neural tissue is disclosed, comprising: providing a neural stimulator including at least one electrode suitable to stimulate neural tissue; testing the impedance of the at least one electrode; calculating an average impedance; calculating a difference from said average impedance for each said at least one electrode; determining bad electrodes based on said difference and a predetermined value; stimulating an electrode of the at least one electrode with at least one test current pulse; taking at least one measurement of an IR drop voltage; calculating a pre-short maximum voltage from at least one IR drop voltage measurement; and comparing the pre-short maximum voltage to a threshold leakage voltage value.

According to a fifteenth aspect, a device is provided for implementing any one of the methods and/or method steps disclosed in the present specification, drawings or claims, is disclosed.

Further embodiments are shown in the specification, drawings and claims of the present application.

BRIEF DESCRIPTION OF THE FIGURES

FIG. 3 is a timing diagram of detecting excessive direct current flow.

FIG. 4 is a schematic of a circuit for detecting build up of low level direct current flow.

FIG. 15 shows sampling points collected by the VPU.

DETAILED DESCRIPTION

The following description includes the best mode presently contemplated for carrying out the present disclosure. This description is not to be taken in a limiting sense, but is made merely for the purpose of describing the general principles of the invention. The scope of the invention should be determined with reference to the claims.

Figure 1:
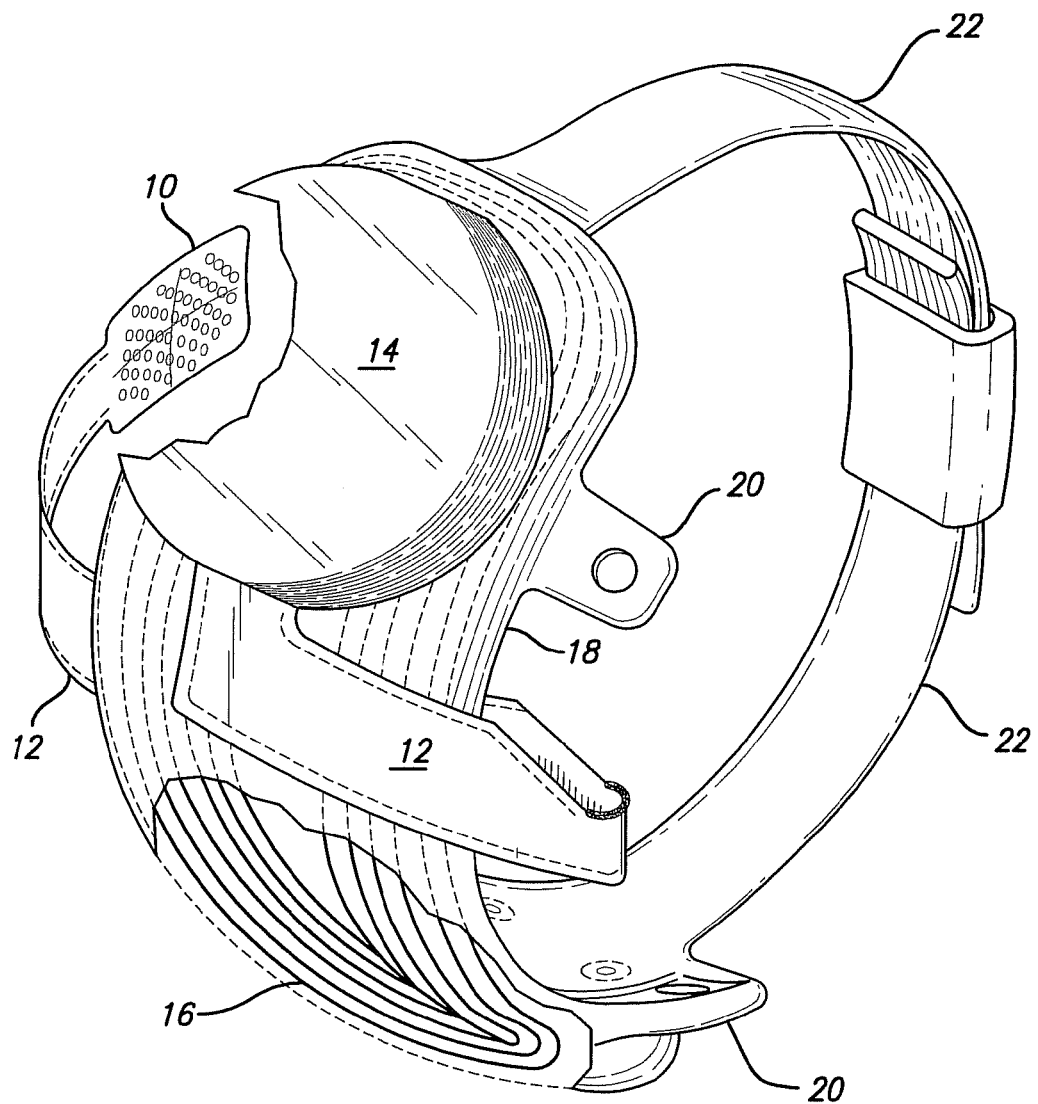
FIG. 1 is a perspective view of the implanted portion of the preferred retinal prosthesis.

FIG. 1 shows a perspective view of the implanted portion of the retinal prosthesis. While the apparatus has broad applicability to neural stimulation, the presented embodiment is a retinal prosthesis. A flexible circuit 1 includes a flexible circuit electrode array 10 which is mounted by a retinal tack (not shown) or similar means to the epiretinal surface. The flexible circuit electrode array 10 is electrically coupled by a flexible circuit cable 12, which pierces the sclera and is electrically coupled to an electronics package 14, external to the sclera.

The electronics package 14 is electrically coupled to a secondary inductive coil 16. Preferably the secondary inductive coil 16 is made from wound wire. Alternatively, the secondary inductive coil 16 may be made from a flexible circuit polymer sandwich with wire traces deposited between layers of flexible circuit polymer. The electronics package 14 and secondary inductive coil 16 are held together by a molded body 18. The molded body 18 may also include suture tabs 20. The molded body 18 narrows to form a strap 22 which surrounds the sclera and holds the molded body 18, the secondary inductive coil 16, and the electronics package 14 in place. The molded body 18, suture tabs 20 and strap 22 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 16 and molded body 18 are preferably oval shaped. A strap 22 can better support an oval shaped coil.

A preferred prosthesis includes an external portion (not shown in FIG. 1, but see FIG. 16) which includes a camera, video processing circuitry and an external coil for sending power and stimulation data to the implanted portion.

Figure 2:
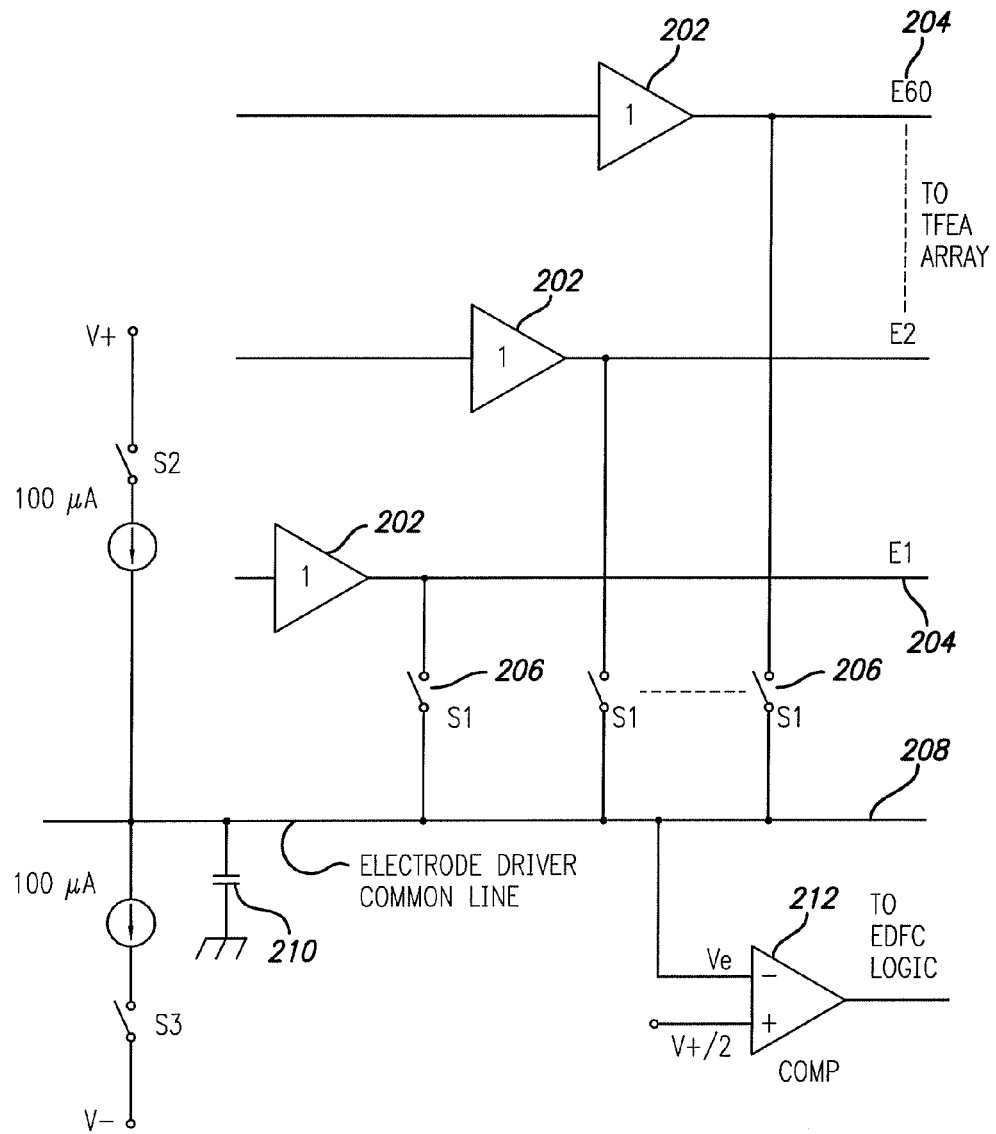
FIG. 2 is a schematic of a circuit for detecting excessive direct current flow.

The electronics package 14 includes an integrated circuit for controlling stimulation. The integrated circuit includes an excessive direct current flow (EDCF) detection circuit as shown in FIG. 2. In the implant or saline environment, a certain amount of continuous DC current passing through an electrode array may cause bubbling which may result in damage to neural tissue. The EDCF circuit detects harmful DC leakage levels and transmits this information through the inductive coil 16 to the external electronics. The integrated circuit in electronics package 14 includes one or more drivers 202, one for each stimulation electrode 204, in the electrode array 10. When the external electronics initiates an EDCF cycle, switches 206 connect each driver 202 to an electrode driver common line 208. Any DC leakage current from the drivers 202 will flow through the electrode driver common line 208. In a fault condition, a leakage could flow through the driver output to either of the power rails, therefore, both sides are tested in alternate stimulation frames. In one particular test, one of the two currents of threshold values is turned on to charge the node capacitor 210 of the common line. The node capacitor 210 is shown with a dotted line because there is no physical capacitor: the node capacitor 210 is the inherent capacitance of the integrated circuit. If there is a leakage path larger than the threshold value in the opposite direction, the potential of the common line is held toward the leakage side. A comparator 212 detects the potential against a predetermined middle potential. The output of the comparator 212 is captured after a predetermined interval, 250 µs for example, which is then interpreted by EDCF control logic. The integrated circuit further includes power switches such that, in case there is an EDCF error (i.e. the DC leakage level exceeds the set threshold, preferably 100 µA), the external electronics will cut off power to the electrode driver circuits and block the leakage source.

FIG. 3, shows the typical timing of the ECDF system. A stimulation cycle 302 is followed by the ECDF cycle 304, followed by a shorting cycle 306. Shorting will bleed off any trace amounts of DC build up.

Electrode bubbling can occur when the voltage across the double layer of the electrode-tissue interface exceeds a threshold voltage window over certain time duration during the stimulation cycles. This threshold voltage window is found to be around ±1.5V for a flexible circuit electrode array 10. Therefore, in an implant environment, the electrode voltage across the double layer shall never exceed this window.

Based on the simplified electrical model of the electrode shown in FIG. 4, the charge buildup on the electrode is reflected with the voltage across the double layer capacitor Cp 402 and resistor $R_p$ 404. During normal stimulation with balanced biphasic current pulses, the maximum voltage across the cap occurs at the end of the first current pulse of amplitude I:

$$V_{Cmax} = IR_p(1 - e^{-Tx/\tau_p}) + V_C(0)e^{-Tx/\tau_p} \approx \quad (1)$$

$$V_C(0) + \frac{Q_x}{C} \text{ (for } t << 1, \text{ and } R_p >> 1\text{)}$$

where Vc(0) is the initial voltage Vsh+ caused by the residue charge left on the capacitor at the end of shorting, $\tau_p = R_p C_p$ is the time constant of the leaky double layer, Tx is the pulse duration (see FIG. 5), and Qx is the total charge of the first stimulation phase flown through the electrode. The electrode-tissue impedance is characterized by $R_S$ 406.

Figure 5:
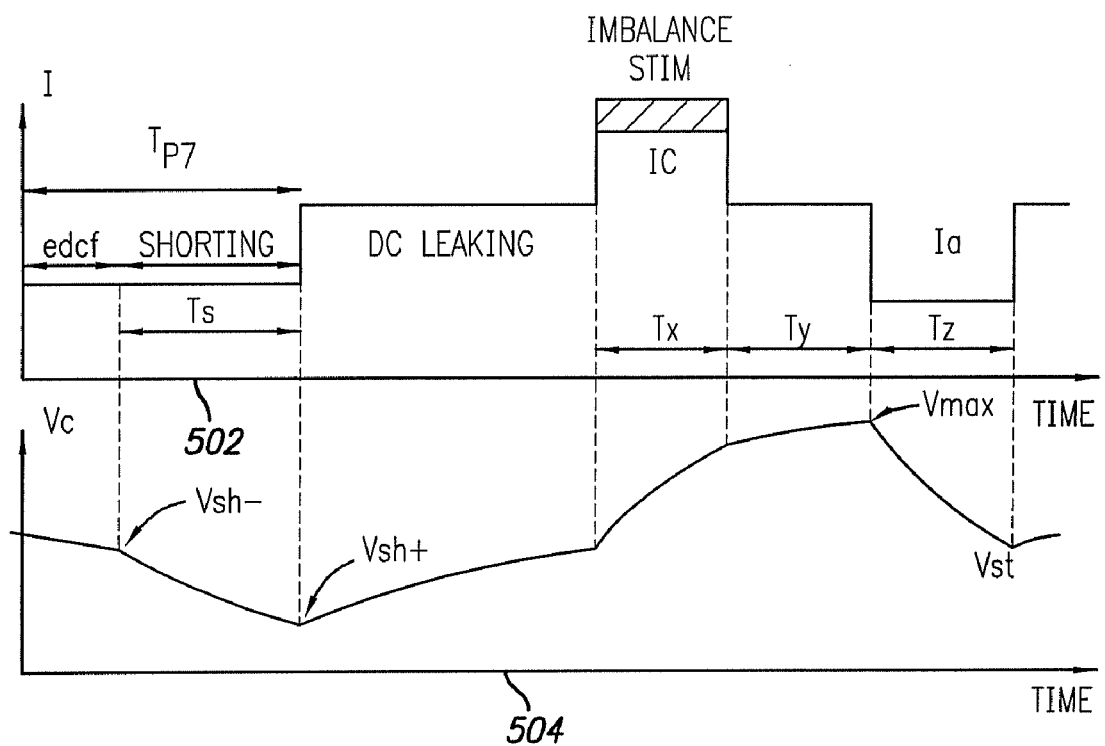
FIG. 5 is a timing diagram of detecting build up of low level direct current flow.

When a DC leakage is present, the charge may increase even when the system is not stimulating. The situation is exacerbated when the DC leakage is in the same polarity as the first phase stimulation current. If the leakage current is small compared to the stimulation current, the voltage build up on the electrode occurs when the stimulating pulse happens just before the shorting starts. In this case, the maximum electrode voltage is at the start of the second current pulse, as illustrated in FIG. 5. The maximum voltage is:

$$V_{Cmax} = I_L R_p + I_S R_p e^{-Tx/\tau_p}(1 - e^{-Tx/\tau_p}) + (V_C(0) - I_L R_p)e^{-(T-T_{P7}-Tx)/\tau_p} \quad (2)$$

where $I_L$ is the leakage current, $I_S$ is the stimulation current, $T_{P7}$ is P7 profile duration (see FIG. 5) that includes a shorting duration of $T_{SH}$=1.4 ms and 0.3 ms for the EDCF check, and T is the stimulation cycle.

A possible electrode voltage map is revealed in FIG. 5, showing a stimulation cycle in the presence of DC leakage that is smaller than the stimulation current. The upper graph 502 is the total current flowing through the electrode and the lower graph 504 is the voltage on the double layer capacitor.

The measured parameters $C_p$ and $R_p$ of the electrodes are preferably 0.25-0.3 μF and 70-80K; but 0.25 μF and 80K to handle the exacerbated condition, which may result in $\tau_p$=20 ms. The shorting time Ts can be set at 1.4 ms for the current embodiment. The stimulation pulse duration Tx may also vary, but the smallest duration should be limited by the implant compliance limit in order to make the electrode less tolerant to leakage. From a 15KΩ electrode impedance assumption, this will allow a 0.275 ms duration at a current of 400 μA (0.35 mC/cm² maximum charge density). The maximum allowed imbalance of 5% should also be put in the equation. Therefore, in an exacerbated condition, we have:

$$\tau_p\text{=20 ms, Tx=0.275 ms, } I_S\text{=400 μA, } T_{P7}\text{=1.4 ms,}$$
$$T\text{=8.3 ms}$$

from which we get:

$$V_{Cmax} = 0.73 V_C(0) + 21.7 I_L(mA) + 0.43(V) \quad (3)$$

This voltage should be kept below 1.5V. For a margin of safety, the maximum allowed electrode voltage across the double layer could be set to $V_{Cmax}$=1.0V.

The steady state value of the residue voltage on the capacitor depends on the shorting duration. It can be estimated as:

$$V_C(0) = V_{SH}(0)e^{-T_{SH}/\tau_S} \quad (4)$$

where $\tau_S$ is the shorting time constant, and $V_{SH}(0)$ is the voltage at the end of the cycle, just before shorting is turned on. In our exacerbated situation, we have:

$$V_{SH}(0) = V_{Cmax} e^{-Tx/\tau_p} - (I_S - I_L)R_p(1 - e^{-Tx/\tau_p}) = 0.72 V_C(0) + 22.5 I_L - 0.06 \quad (5)$$

where $\tau_S = R_{IR} C_P$=15K×0.25 uF=3.75 ms.
Therefore, with $T_{SH}$=1.4 ms, we have from equations (4) and (5):

$$0.73 V_C(0) - 22.5 I_L + 0.06 = 0 \quad (6)$$

From equations (3) and (6), we can calculate the maximum allowed as $$I_{L\,max} = 12 \text{ μA} \quad (7)$$

This maximum allowable leakage current for an individual electrode to ensure that it does not causing electrode bubbling is lower than the EDCF detection circuit (described in reference to FIGS. 2 and 3) threshold current which addresses the total leakage current of all channels. Therefore, a test is needed to detect if the leakage level of an individual channel passes the maximum allowed leakage value $I_{Lmax}$ estimated.

The electrode potentials takes some time to stabilize because the time needed to reach the balance between the charge released by shorting and the build up by charge imbalance or leakage. The above analysis on electrode voltages only addresses the steady state condition. Because a DC leakage is typically considered persistent current flow with or without the presence of stimulation, one method used is to measure the electrode voltage caused by the leakage current in quiescent condition in which all stimulation is turned off. This way the disturbance on the electrode voltage caused by the stimulation currents is avoided. However, the electrode voltage caused by the leakage current $I_L$ (if existent) is still a function of the shorting duration. When we use the same shorting strategy as the normal condition with EDCF turned off, i.e., $T_{SH}=T_{P7}$=1.7 ms, the steady state voltages on the electrode double layer are estimated as:

$$V_{SH-} = V_{SH+} e^{-(T-T_{P7})/\tau_p} + I_L R_p(1 - e^{-(T-T_{P7})/\tau_p})$$
$$\approx 0.718 V_{SH+} + 22.5 I_L \quad (8)$$

$$V_{SH+} = V_{SH-} e^{-T_{SH}/\tau_S} \approx 0.635 V_{SH-} \quad (9)$$

Which give us:

$$V_{SH-} = 0.50 V; V_{SH+} = 0.32 V$$

Where $V_{SH-}$ and $V_{SH+}$ are the voltages immediately before Vsh− and after Vsh+ the shorting pulse. Either $V_{SH-}$ or $V_{SH+}$ can be used as the individual electrode leakage threshold; however, $V_{SH-}$ is preferred because of its higher value for better accuracy of the measurement. The voltage driver output $V_{DO}$ is the sum of the I-R drop caused by the real part of the electrode-tissue impedance $R_S$ 406 and the electrode voltage on the double layer capacitor $V_C$ discussed supra. The I-R drop can be calculated as $I_L R_{ir}$, where $R_{ir}$ is the electrode impedance.

From (7), the I-R drop caused by the allowed maximum DC leakage current is $I_{Lmax} R \approx 0.12$-0.56V constant for electrode impedances ranging 10-40KΩ. However, when the electrode is lifted from the retina, the impedance could be lowered to be as low as 3KΩ. For a relatively accurate estimation of the leakage current using the $V_{DO}$ measurement, the I-R drop should be subtracted from the $V_{DO}$ result using the pre-measured electrode impedance values. For simplicity, it may be preferable to ignore the I-R drop effects in this leakage detection protocol and directly use the $V_{DO}$ data as the electrode voltage $V_C$. Ignoring the I-R drop will yield an approximately 20-50% inaccuracy of the leakage value estimation that will result in a more conservative monitoring. This should not compromise the safety and should simplify the measurement.

In the suggested electrode impedance measurement protocol, an electrode with impedance 65KΩ or higher is labeled as an open electrode. Stimulation to an open electrode is turned off. However, an electrode with impedance higher than 65KΩ could still bubble because of DC leakage. Assuming that the maximum allowed leakage is still 12 μA and the compliance limit for the leakage current is 7.0V, calculating with the same method used above it is shown that an electrode with impedance value as high as 450KΩ could reach electrode bubbling status. However, the measured voltage would be limited to about 4V on the anodic side, which should limit the detectable threshold leakage to electrodes with impedance up to 230KΩ. For example, if the measured electrode impedance is 200KΩ, then a measured $V_{DO}$ of 3.4V or more can be considered a bubbling status. In either case, the electrode impedance measurement should be able to discriminate between a high impedance electrode and an open electrode.

The following two-step method is suggested to label an electrode as a high impedance (HI) electrode: (a) After the regular impedance measurement routine, all "open" electrodes (if any) are measured again using 8.1 μA/1 ms current pulses with the $V_{DO}$ sampling point set at 0.9 ms after the pulse start. (b) An electrode with measured impedance 500KΩ or less ($V_{DO}$<±4V) shall be tagged as HI electrode, while higher impedance electrodes are tagged as open.

For HI impedance electrodes, the build up voltage on the electrode capacitor is solely from DC leakage because they are not stimulated. Therefore, the maximum allowed electrode voltage is $V_{SH-}$=1V, plus the I-R component when using $V_{DO}$ measurement. Therefore, the threshold for an HI electrode should be $V_{DO}$ (measured at $V_{SH-}$):

$$VDO|_{V_{SH-}} <= I_{L\,max}R+1 \approx 0.012R(K\Omega)+1 \quad (10)$$

Considering the limited ADC range in the anodic direction, it may be preferable to check all HI electrodes with impedance 200KΩ or higher against the threshold voltage of 200KΩ, which is 3.4V. For open electrodes, this checking procedure may be omitted.

Figure 6:
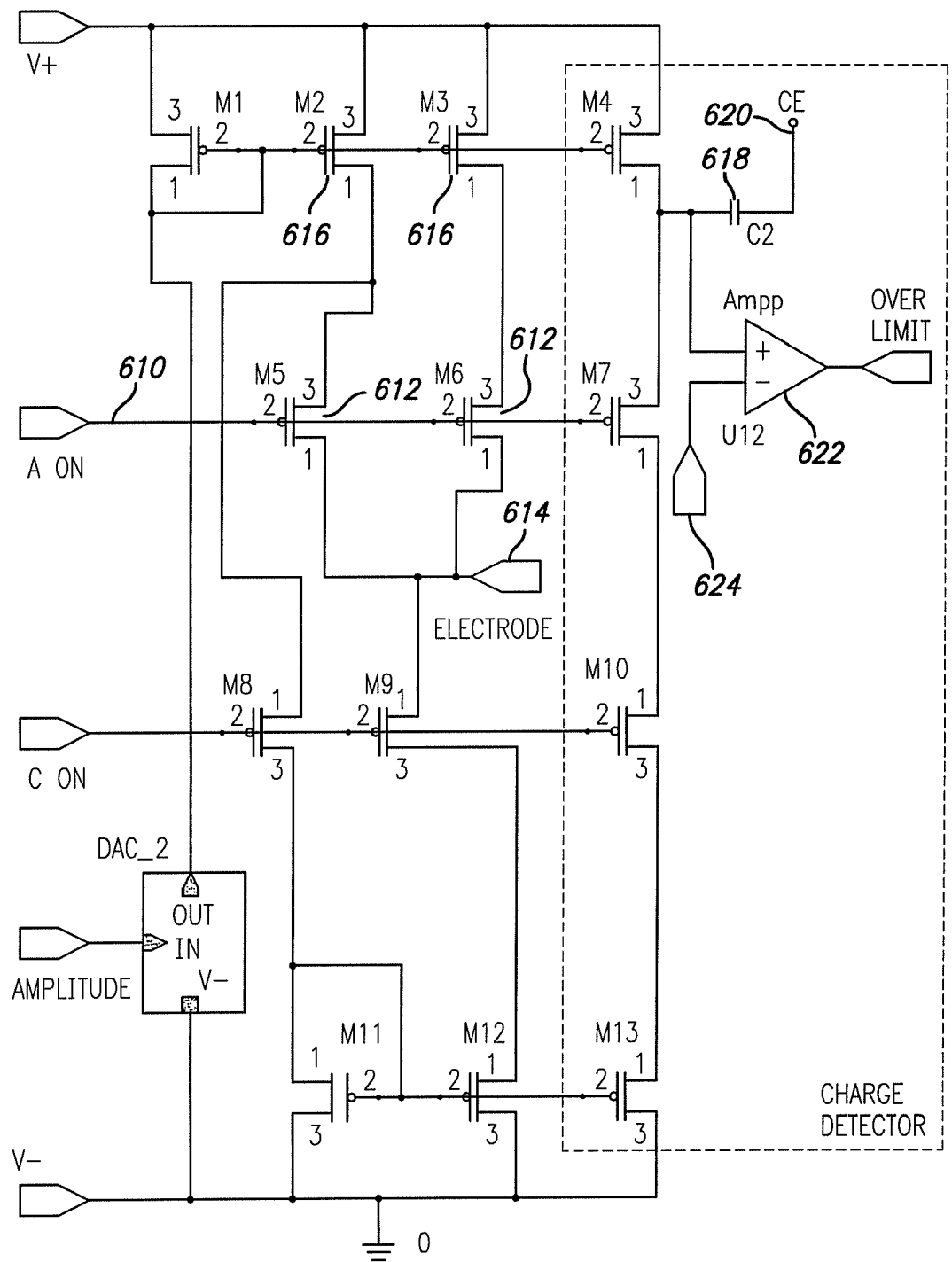
FIG. 6 is a schematic of a circuit to detect exceeding a maximum charge per phase.

Referring to FIG. 6, the problem of exceeding maximum charge per phase (MCPP) can be solved with two different methods. In one case, the cathodic and anodic pulse amplitude of each electrode is multiplied by the phase duration and the result is checked against a predetermined MCPP value. If the value is exceeded, the amplitude value is clipped to achieve the limit. This first method is accurate for square waves, but becomes less accurate as the stimulation wave form becomes arbitrary. In another method, a discrete integral is taken in the time representation of the pulse to calculate the charge. If the integral at any point of time exceeds the absolute MCPP value (positive or negative), the amplitude value is either clipped to achieve the limit or zeroed out. Another method that could be used is by utilizing an active current monitor on the stimulator device, which limits the current to a particular MCPP. For all these methods, the implementation should be stimulator setting dependant (e.g. frequency setting) so that the safety checks should adapt to limit the charge to the MCPP in any case.

The circuit shown in FIG. 6 performs an integration of the waveform through capacitance charge. The stimulation signal 610 is amplified in transistors 612 to drive the stimulating electrode 614. Simultaneously, the stimulation signal 610 is amplified in transistors 616 to create a much smaller, but proportional charge signal. Capacitor 618, between the charge signal output and the common electrode 620 is charged by the charge signal. Comparator 622 compares the charge on capacitor 618 with a predetermined maximum charge 624 and generates an over limit signal when the charge on capacitor 618 is over the predetermined maximum charge.

Another way to limit current density is to provide a compromise between the monopolar mode and bipolar mode of stimulation. The method includes setting up stimulation wave forms as in bipolar stimulation mode without disconnecting the common electrode (ground). A portion of the current will flow between the electrodes, and a portion of the current will flow between the electrodes and ground. The ratio of current flow will depend on electrode impedance. This hybrid bipolar mode of stimulation could possibly result in lower thresholds than can be obtained from a true bipolar mode of stimulation, and also has the advantage of greater selectivity than can be obtained from a monopolar mode of stimulation. To set up a safe hybrid bipolar stimulation wave form, the two electrodes concerned should have balanced biphasic currents going in opposite phases at exactly the same times, with the common electrode connected. If the pulse waveforms are balanced by themselves on each electrode but overlap non-contiguously in opposite phases with other electrodes in the array, a resultant unbalanced current could flow through the tissue eventually causing neural tissue damage. A safety check method could be implemented in the external electronics to prevent such unbalanced multipolar waveforms to be sent to the stimulator. The above phenomenon and safety check method is also applicable to multipolar forms of stimulation (i.e. in addition to bipolar).

It is also important to limit the maximum stimulation across all electrodes in an electrode array. While each electrode is individually stimulating at a safe level, there can still be neural damage, or even in some cases pain, if all electrodes are stimulating at or near their individual maximum level. Hence, it is important to track and limit the sum total stimulation from all electrodes, which can be performed by a calculation. For each stimulation cycle, all stimulation values are summed and compared with a predetermined maximum. If the sum exceeds the predetermined maximum, the stimulation is reduced, either proportionally across all electrodes, or by limiting electrodes set to higher stimulation levels. This calculation can be performed by software in the external electronics.

Broken electrode detection can be achieved with a method of monitoring impedance of the electrodes (over time (ΔI), as well as comparing impedances of electrodes to its neighboring electrodes in the media, and incorporation of physiological data as observed from physicians). When a broken electrode is found in the system, the stimulator device is commanded to halt stimulation on that broken electrode—with the history of electrode damage logged and persistent in the stimulator controller. Visually, the electrode health is represented through a color/topographical map of the electrode array on a computer system. Optimally, a movie-like data playback of the impedances can be provided. Electrode damage can also consist of shorting between electrodes (as opposed to 'broken') which will also be detected through impedance monitoring.

Charge imbalance can be reduced by implementing a 1.4 ms (adjustable, as mentioned previously) shorting pulse prior to any stimulation on every stimulation frame of the stimulator. Additionally, the stimulator controller can adjust and check the anodic and cathodic current level, using amplitude parameter tables determined from the manufacturing tests of the stimulator, to achieve the best balance. The stimulator controller also checks that there exist no overlapping anodic/cathodic profiles that could cause a charge imbalance at the tissue.

Another method of reducing charge imbalance on an electrode is by having the stimulator controller auto-balancing the pulse. Two ways of achieving this are by appending a square pulse after the pulse to compensate for the imbalance or by appending an inverted pulse to compensate. A check against DC flow in tissue from the electrodes is achieved through a combination of the ASIC test, the shorting function, and an initial individual electrode check implemented on startup (or periodically) by the stimulator controller. The issue of implant overheating is handled in multiple ways. Power is controlled on the retinal prosthesis through a feedback loop fed by implant back telemetry. In one embodiment, this is achieved by inferring the implant heat through the current in the shunt regulators of the implant device. However, if a thermistor is placed in the implant device, then the heat can be measured and returned to the controller through the back telemetry link.

Additionally, the instantaneous current output on the stimulator device can be limited to a constant value by the controller. This ensures that no amount of instantaneous current is allowed that might expect the stimulator to reset due to lack of power. This instantaneous current limit could also be variable (instead of constant) with appropriate back telemetry and controller design. For system operational modes that do not allow heat control via the shunt current values, the controller performs a check that ensures the implant shunt current level can be set to a safe value immediately prior to the operational mode which doesn't provide shunt current information in the back telemetry. In addition, the stimulator controller verifies the voltage setting with an ADC circuit upon any change of voltage to the RF power circuitry.

Figure 7A:
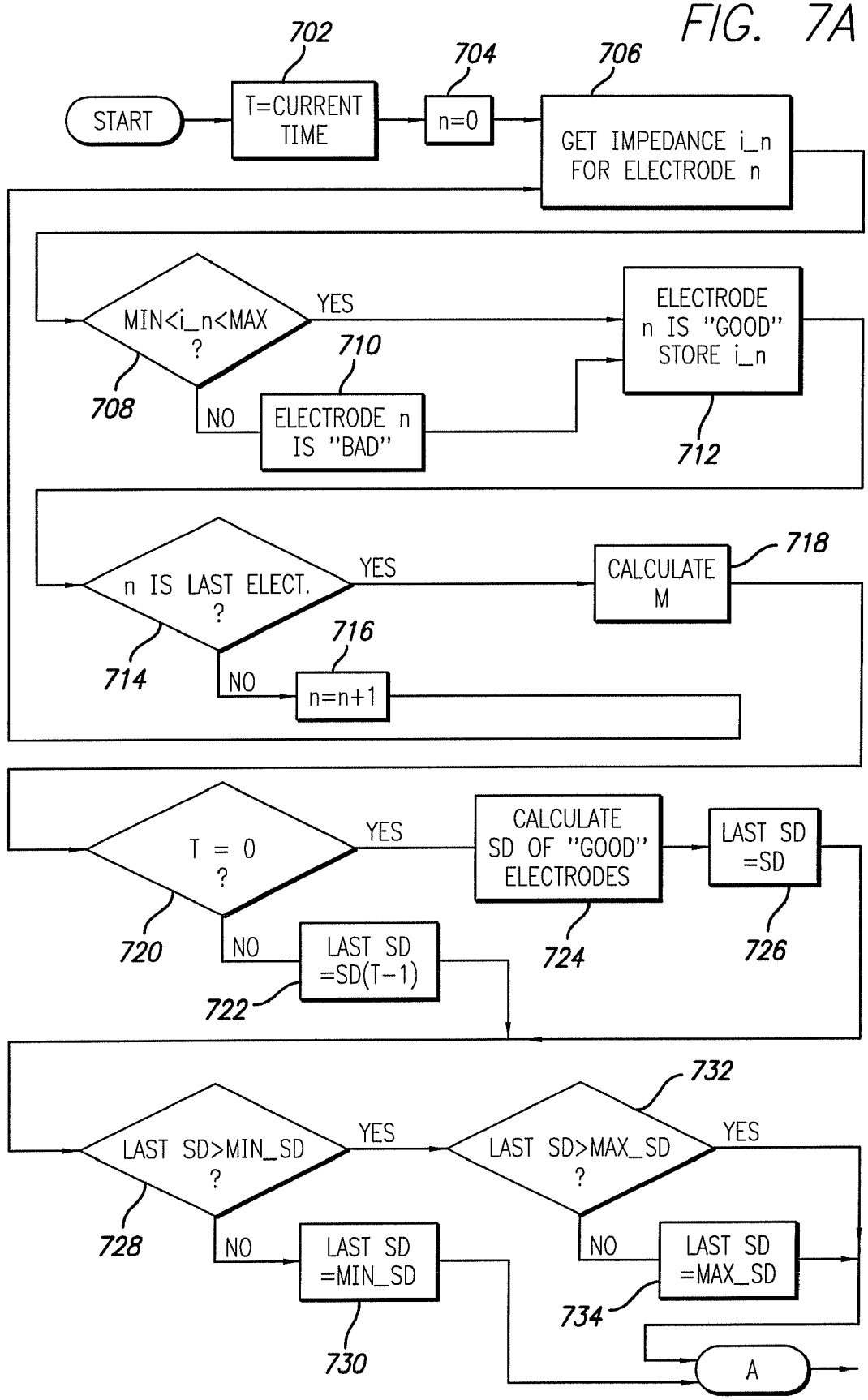
FIGS. 7A and 7B are flowcharts depicting a method for identifying defective electrodes.

Referring to FIG. 7A, one embodiment of the electrode failure detection system includes a table of electrode impedance value that is N, the number of electrodes, by T, the time history stored, and a table of electrode state values with three states, good, questionable, and bad. Each test should begin by loading a time value 702 to identify the test. The electrode counter is set to zero 704, and the first electrode is tested 706. The system determines if the electrode impedance is within hard limits 708. These limits are the same for all electrodes. This can be used to catch the most obvious failures. As an illustration, the impedance value returned can range from 0Ω (complete short) to 65,535Ω (complete open), where the nominal value for a good electrode might be in the range of 10,000Ω to 20,000Ω. Here, a lower limit of 2,000Ω and an upper limit of 50,000Ω could be used, where any electrode falling outside these ranges would be defined to be experiencing a failure and will be marked bad 710. If the electrode is within the hard limits, the electrode impedance is stored in the table 712. The process is repeated 714 incrementing the electrode counter 716 each time.

Once all electrodes have been tested, the system can calculate and store a median and a standard deviation 718. If this test has been previously preformed 720, the impedance data is shifted to the next memory location 722. If not, calculate the standard deviation of good electrodes 724, and shift the standard deviation to the previous memory location 726. If the electrode values are close, a very low standard deviation might trigger too many electrodes marked as bad. Therefore, the standard deviation can be compared with a preset minimum 728 and replaced with the minimum if the minimum is higher 722. If the electrode values are far apart, a very high standard deviation might not mark bad electrodes. Therefore, the standard deviation is compared with a preset maximum 730 and replaced with the maximum if the maximum is not higher 732, 734.

It has been observed that an electrode which fails (for example, reading as high as 65 kΩ initially) may give subsequent impedance values which begin to fall, sometimes returning to a nominal, good value. This is apparently due to fluid leaking in the broken area and creating an alternative (and undesirable) conduction path. Therefore, any one set of readings might not show all electrodes known obviously to be broken, so a history should be maintained. If an electrode ever exceeds the limits, it could be considered permanently failed.

The history of the electrodes should not begin until the implantation of the array has stabilized. Impedance readings are very useful through the implantation process, but values could shift drastically, and false failures can impede the process.

It might appear that many failed electrodes never reach a high value, or reach it and return so quickly it may not be recorded. Therefore, additional checks are suggested.

Figure 7B:
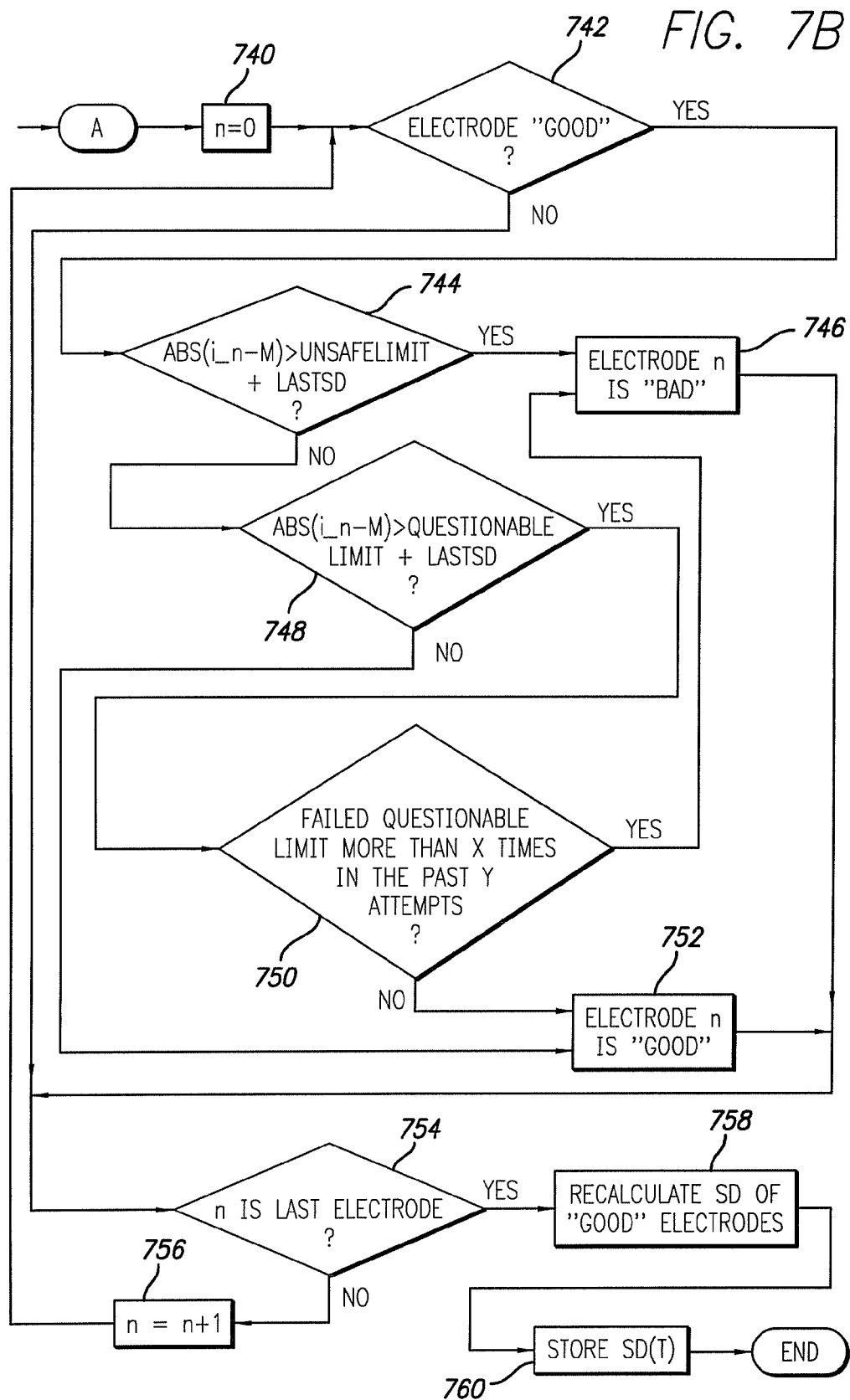

Referring to FIG. 7B, the electrode counter is again set to zero 740. If the electrode is already marked bad 742, it should not be marked good again. If the absolute value of the impedance of an electrode minus the median impedance of all the electrodes is greater than an unsafe limit times the standard deviation 744, the electrode marked bad 746. Otherwise, the electrode is marked good 752. For example, the unsafe limit can be set to be four times the standard deviation. If the absolute value of the electrode impedance minus the median is greater than a questionable limit times the standard deviation 748 and the electrode has measured questionable a predetermined number of time previously 750, the electrode is marked as bad 746. For example, the questionable limit can be three times the standard deviation. The process should be repeated until all electrodes have been checked 754, with the electrode counter incremented each time 756. Finally, the standard deviation can be recalculated for the remaining good electrodes 758 and stored 760.

In one embodiment, impedance is used to determine the electrode integrity at the interface of the neural stimulator and tissue, as well as the integrity of the electrode stimulation path through the implantable device. However, data obtained both in vitro and in vivo seem to indicate that these impedance readings are time dependent, and any given temporal snapshot might show failed electrodes as having perfectly nominal values. Furthermore, potentially critical failures such as electrode movement or loss of tissue contact might not be quickly diagnosed using the current methods as the changes in impedance might not be large.

Figure 8A:
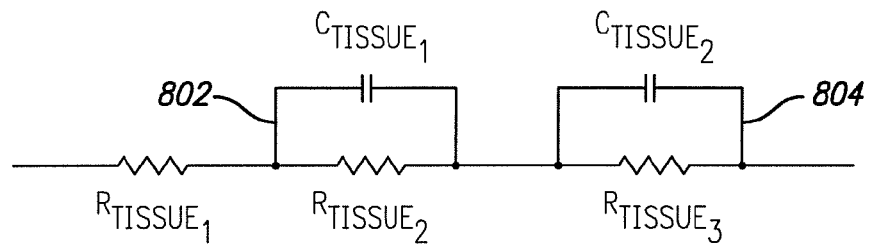
FIGS. 8A and 8B are schematic representations of the electrode tissue interface.
Figure 8B:
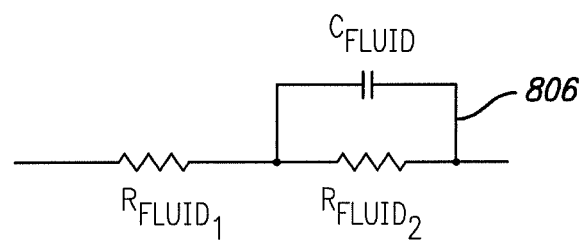
Figure 9A:
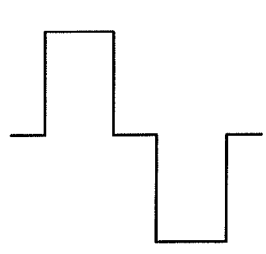
FIGS. 9A-9E are wave forms illustrating the effects of altering the electrode tissue interface.
Figure 9B:
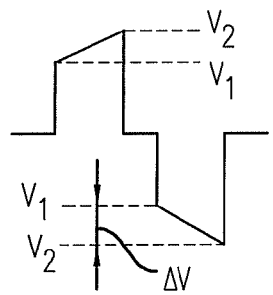
Figure 9C:
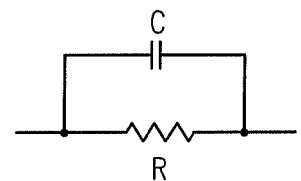
Figure 9D:
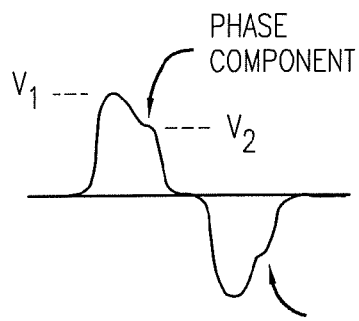
Figure 9E:
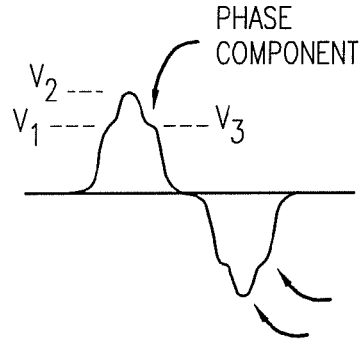

Capacitance measurement is one possible solution to this limitation, because electro-neural interfaces have distinct capacitive characteristics. Referring to FIG. 8A, an interface between an electrode and tissue is actually two interfaces, one from electrode to fluid 802 and a second from fluid to tissue 804. However, when an electrode lifts off tissue, the resulting circuit resembles a single electrode fluid interface 806 as shown in FIG. 8B. When an electrode is making good tissue contact, it typically follows the tissue model shown in FIG. 8A, with an average value of 15 k-25 kΩ. When an electrode has completely lifted-off, it generally follows the fluid model shown in FIG. 8B. It is designated 'fluid' since the values and characteristics of an implanted array lifted up in fluid are the same as that in saline in the laboratory.

When an electrode begins to lift off, it begins making contact with the fluid, and thus has two parallel impedance paths. A simple impedance measurement should show only a slight drop at the beginning. However, the phase characteristics of the two paths are different, in both total capacitance value and total phase shift. Thus, a waveform reading should show the effect of the loss of contact.

FIG. 9 shows a simple model for how a capacitor would affect an AC square wave. Initially, it may appear simple to measure $V_2$ and $V_1$ and establish $\Delta V$ as $V_2-V_1$, and thus find a measurement of the capacitance, as $\Delta V$ would increase as the total capacitance in the circuit increases. However, as given in the schematic of a typical electrical model of the electrode-tissue interface, FIG. 8A, the portion of electricity going through the capacitor is phase shifted by 90°. The resultant waveform does show a capacitive phase shift, but with rounded peaks potentially anywhere on the waveform: therefore, $\Delta V$ would not be an accurate measure of capacitance. A method that accounts for this phase shift should be utilized; one which could reflect the total capacitance as well as reveal changes in its characteristics.

The difference in capacitance between the various electrical paths which occurs in both healthy and failed electrodes can be manifested as a phase difference in the various waves that sums the resultant measured waveform. This difference can be computed for each stimulation phase, based on the area of the curve of the first derivative, subtracting the baseline waveform where no phase shift is present. Healthy electrodes appear to have distinctive measurable characteristics in both anodic and cathodic phases. These characteristics change significantly when an electrode is losing contact at the neural interface (array lift-off) or is degrading, and thus electrodes which show a significant difference in phase shift are likely experiencing the manifestation of a failure. This method could be used to detect array lift-off potentially before it would be detected by the associated impedance values currently in use.

Another embodiment of low level leakage detection mechanism is based on the electrode properties and the electrode model will now be disclosed. An algorithm can be used to achieve low level leakage current measurement for every electrode with a general purpose voltage measurement mechanism. The method according to this embodiment also facilitates external control of the detection; therefore, the control can be easily updated. Based on the simplified electrical model of the electrode shown in FIG. 4, it can be seen that the charge buildup on the electrode is reflected with the voltage across the double layer capacitor $C_P$. When a current I, either a stimulating current pulse or a DC leakage current, flows through it, a voltage $V_c$ is built up across the capacitor $C_P$ during a period of time t, which can be estimated as $$V_C = V_C(0)e^{-t/\tau_P} + IR_P(1-e^{-t/\tau_P}) \quad (11)$$

where $V_C(0)$ is the initial voltage caused by the residue charge left on the capacitor at the end of shorting, $\tau_p=R_pC_p$ is the time constant of the leaky double layer of the electrode-tissue interface.

When there is no current flow through the electrode, the residue charge previously built across the double layer capacitor $C_P$ 402 (see FIG. 4) decays slowly through the leaky path $R_P$ 404, as quantified by the voltage:

$$V_C = V_C(0)e^{-t/\tau_p} \quad (12)$$

Figure 10:
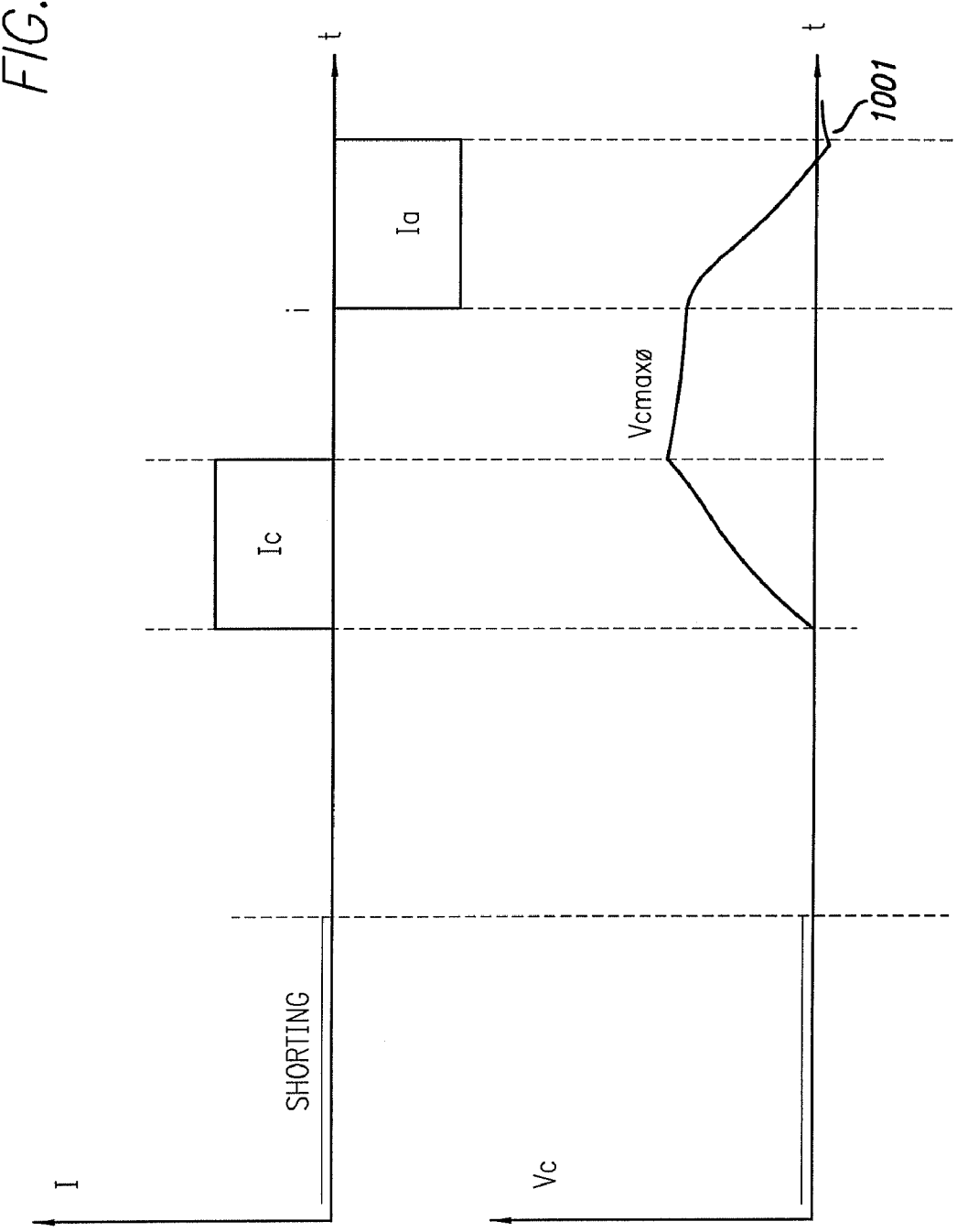
FIG. 10 shows biphasic stimulation and the voltage build up across the electrode double layer capacitor.

During biphasic stimulation, as shown in FIG. 10, the charge on $C_P$ 402 (see FIG. 4) is built up during the first phase of stimulation, leaked through $R_P$ 404 slowly during the quiet inter-phase period, and released by the reverse current during the second phase, with a little overshoot 1001 at the end of stimulation. From FIG. 10, it is seen that the maximum voltage across the capacitor, $V_{Cmax0}$, occurs at the end of the first pulse. When a DC leakage is present, however, the charge on the capacitor is built up even when the electrode is not being stimulated. The worst case is when the DC leakage is in the same polarity as the first phase stimulation current, such that the effects of the stimulation current and the DC leakage add up in building up the double layer voltage. If the leakage current is small compared to the stimulation current, which is the case in the low leakage scenario, the exacerbated case voltage build up on the electrode occurs when the stimulating pulse ends just before the shorting starts, as seen in FIG. 5.

When the stimulating pulse ends just before the shorting starts, the maximum electrode voltage, $V_{Cmax}$, occurs at the start of the second current pulse. Factoring in an exacerbated case imbalance of 5% between the two phases of the stimulation current, the maximum allowed DC leakage current $I_{Lmax}$ that will keep the electrode voltage at below a threshold value of $V_{Cmax}$ can be calculated as:

$$I_{Lmax} = \frac{(1-e^{-T_{SH}/\tau_S}e^{-(T-T_{SH})/\tau_P})V_{Cmax} - (1-0.95e^{-T_{SH}/\tau_S}e^{-(T-T_{SH}-2T_X)/\tau_P})e^{-T_X/\tau_P}(1-e^{-T_X/\tau_P})R_P I_{STIM}}{\left[\begin{array}{c} e^{-2T_X/\tau_P}(1-e^{-(T-T_{SH}-3T_X)/\tau_P})+ \\ (1+e^{-T_X/\tau_P}+e^{-T_{SH}/\tau_S}e^{-(T-T_{P7}-T_X)/\tau_P})(1-e^{-T_X/\tau_P}) \end{array}\right]R_P} \quad (13)$$

where $\tau_p$ is the time constant of the electrode double layer $\tau_p=R_pC_p$, $\tau_S$ is the time constant of the electrode shorting path $\tau_S=(R_S//R_p)C_p$, $I_{STIM}$ is the stimulation current, $T_X$ is the pulse duration of the stimulation current pulses which is assumed to be biphasic with a "1+1+1" profile arrangement (i.e., the pulse duration of cathodic pulse Tx is equal to the pulse duration of the anodic pulse Tz and is also equal to the delay between the cathodic and anodic pulses Ty), $T_{P7}$ is the profile duration $T_{P7}$ that includes a duration of $T_{SH}$ for shorting following a duration of common electrode disconnection for the EDCF check in the preferred embodiment, and T is the stimulation cycle.

Equation (13) shows that, for a predefined safe $V_{Cmax}$ value, the DC leakage threshold $I_{Lmax}$ is inversely affected by the stimulation current $I_{STIM}$, the stimulation pulse duration $T_X$, the time constant of the electrode double layer $\tau_p=R_pC_p$, and the time constant of the shorting path $\tau_S=(R_S//R_p)C_p$. Among them, $I_{STIM}$ and $T_X$ are application parameters, $R_p$ and $C_p$ are design parameters, while $R_S$ is tissue related parameter.

The electrode parameters $C_p$ and $R_p$ of the electrodes can typically be 0.25-0.3 µF and 80-100K; for example, they can be 0.25 µF and 100K to handle less favorable conditions where $\tau_p=25$ ms. $T_{SH}$ is set to 1.44 ms and $T_{P7}$ to 1.7 ms in the present embodiment. In use, the stimulation current $I_{STIM}$ and pulse duration $T_X$ vary constantly. However, the exacerbated condition is still limited by the maximum charge density per phase of the electrode, which is 0.35 mC/cm² in the present embodiment, the maximum compliance of the electrode driver, which is set to 6V in the present embodiment, and the stimulation cycle T, which is set to 8.3 ms in the present embodiment. The compliance voltage generated from the stimulation also depends on the tissue and electrode impedance that is a combination of $R_S$, $R_P$, and $C_P$. Substituting with the predefined time parameters, the following equation is obtained:

$$I_{Lmax} = \qquad (14)$$

$$\frac{(1 - e^{-1.44/\tau_S} e^{-6.86/\tau_P})V_{Cmax} -}{[e^{-2T_X/\tau_P}(1 - e^{-(6.6-3T_X)/\tau_P}) +} \\ (1 - 0.95 e^{-1.44/\tau_S} e^{-(6.86-2T_X)/\tau_P}) e^{-T_X/\tau_P}(1 - e^{-T_X/\tau_P})R_P I_{STIM}}{(1 + e^{-T_X/\tau_P} + e^{-1.44/\tau_S} e^{-(6.86-T_X)/\tau_P})(1 - e^{-T_X/\tau_P})]R_P}$$

An example value estimation can have a measured $R_S$ of 15KΩ, $R_P$ of 100KΩ, and $C_P$ of 0.25 μF. Therefore, $\tau_P$=25 ms and $T_S$=3.3 ms in the example. The exacerbated situation stimulation can be $I_{STIM}$ at 370 μA and $T_X$ at 300 μs, where the stimulation current reaches the maximum charge density and the output voltage hit the compliance limit at the end of the pulse. Adding a safe margin in both the estimation and application, the threshold voltage $V_{Cmax}$ can be set to 1V. Substituting these values into the $I_L$ equation provides a DC leakage threshold of 12 μA for this electrode.

It can be difficult to directly monitor the small DC leakage on each electrode. However, the relationship between the DC leakage current and the electrode voltage, $V_E$, which is the sum of electrode capacitor voltage $V_C$ and the I-R drop through the series resistance of the electrode tissue interface can be determined. This voltage is detectable at the electrode driver output in the implant condition. In order to estimate the leakage current level using the electrode voltage measurement, predefine the shorting duration and frequency the same as the condition used in the above analysis and measure the electrode voltage at the driver output in a predefined point after the electrode reaches its steady state.

Figure 11:
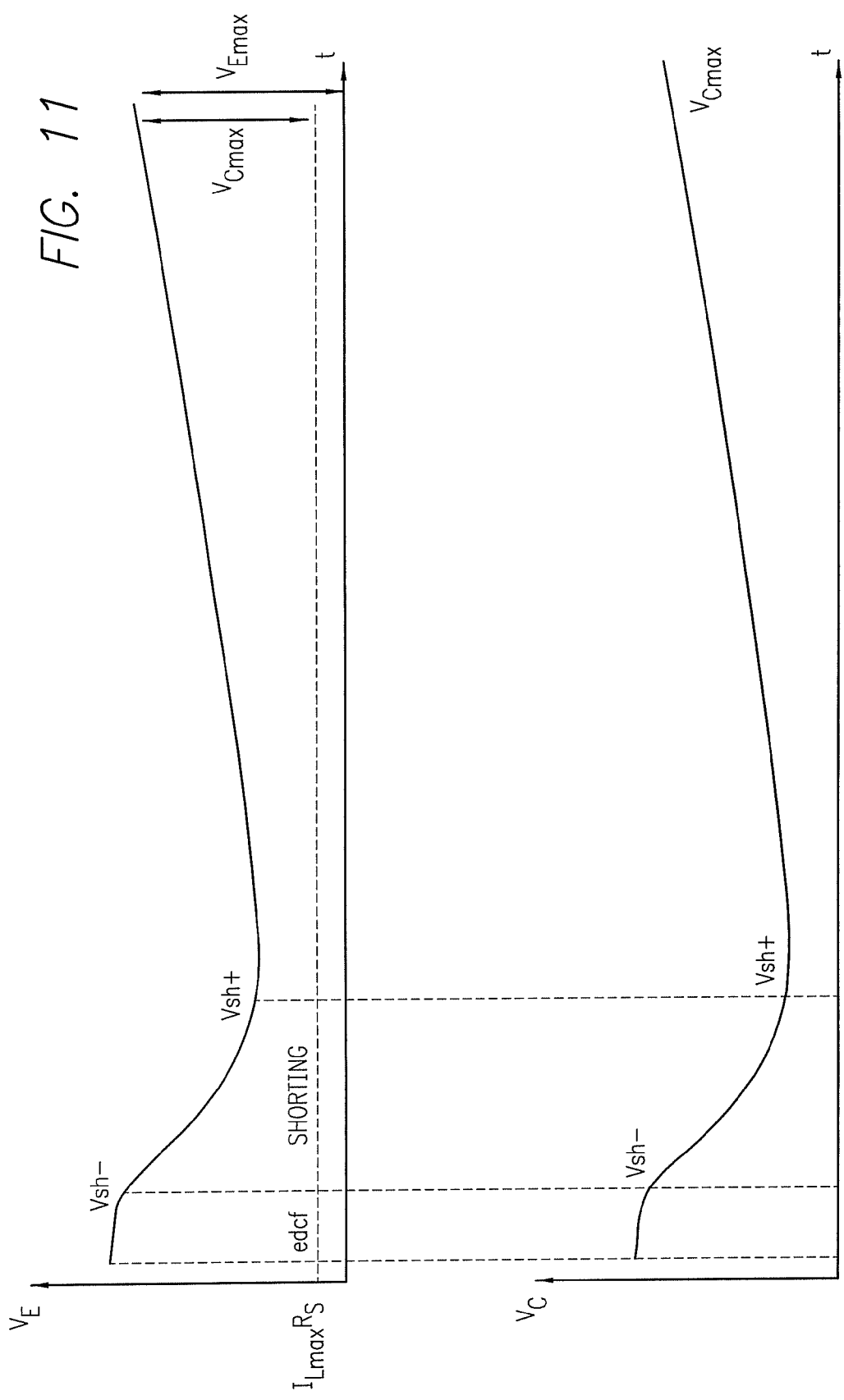
FIG. 11 shows the electrode voltage maps, $V_E$ for the voltage on the electrode double layer capacitor and $V_C$ for the voltage at the electrode driver output, caused by DC leakage only.

It should be noted that the test described above is used to estimate the voltage caused by the leakage current in the absence of any stimulation current. The electrode voltage map induced by the DC leakage current is shown in FIG. 11. For a maximum sensitivity, set the measurement point right before the shorting begins. In this condition, the $V_E$ threshold value is:

$$V_{Eth} = I_{Lmax}\left(R_S + \frac{R_P(1 - e^{-6.6/\tau_P})}{(1 - e^{-1.44/\tau_S} e^{-6.86/\tau_P})}\right) \qquad (15)$$

Figure 12:
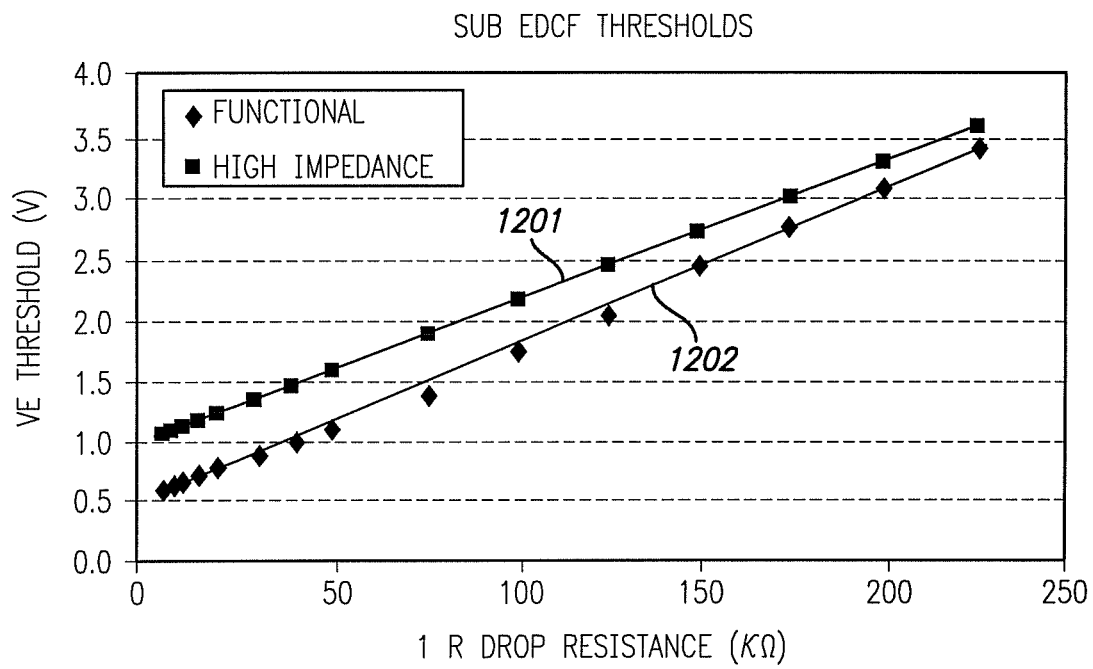
FIG. 12 is the sub-EDCF electrode voltage threshold vs. I-R drop resistance of the electrode-tissue interface.

Therefore, the DC leakage current threshold current $I_{Lmax}$ is converted to an electrode voltage threshold $V_{Eth}$. In the previous example, the threshold voltage from 12 μA threshold current will be 0.75V. In use, this threshold voltage can be pre-calculated from equation (15) for a range of normal electrode/tissue impedances, as exampled in FIG. 12. FIG. 12 shows example pre-calculated voltages for given impedances of high impedance electrodes 1201 and of functional electrodes 1202.

When an electrode appears to have high impedance, it either has severed its connection internally from the driver or has lost effective electrode surface area interfacing with the tissue. In the first case, which shows very high impedance, DC leakage will not cause bubbling of the electrode, and therefore poses minimal safety concern. In the second case, however, DC leakage will affect the electrode in the same way as a normal electrode. When a high impedance electrode is detected, the electrode should be turned off so that no stimulation current is applied and the build up voltage on the electrode capacitor is solely from DC leakage. Therefore the DC leakage threshold does not include the effect of stimulation ($I_{STIM}$, $T_X$) in equation (15). With similar analysis, we have the leakage threshold for high impedance electrodes where the electrode is turned off:

$$I_{Lmax} = \frac{(1 - e^{-1.44/\tau_S} e^{-6.86/\tau_P})V_{Cmax}}{(1 - e^{-6.6/\tau_P})R_P} \qquad (16)$$

A $V_{Cmax}$ value of 1V can be applied to the high impedance electrodes to estimate the leakage threshold $I_{Lmax}$. The voltage threshold $V_{Eth}$ can be calculated from equation (15) with the $I_{Lmax}$ value from equation (16). However, a high impedance electrode can have smaller double layer capacitance value $C_P$ because of the reduced effective surface area. For this reason, the nominal $C_P$ value of high impedance electrodes is much smaller than a normal electrode. Assuming a nominal $C_P$ value of 0.05 μF, the threshold voltage calculated using equation (15) for high impedance electrodes is shown in FIG. 12 as the High Impedance curve 1201. For open electrodes that are electrically detached from the electrode driver, the DC leakage path is also discontinued and, therefore, the capacitance checking procedure may be omitted for those electrodes.

Figure 13:
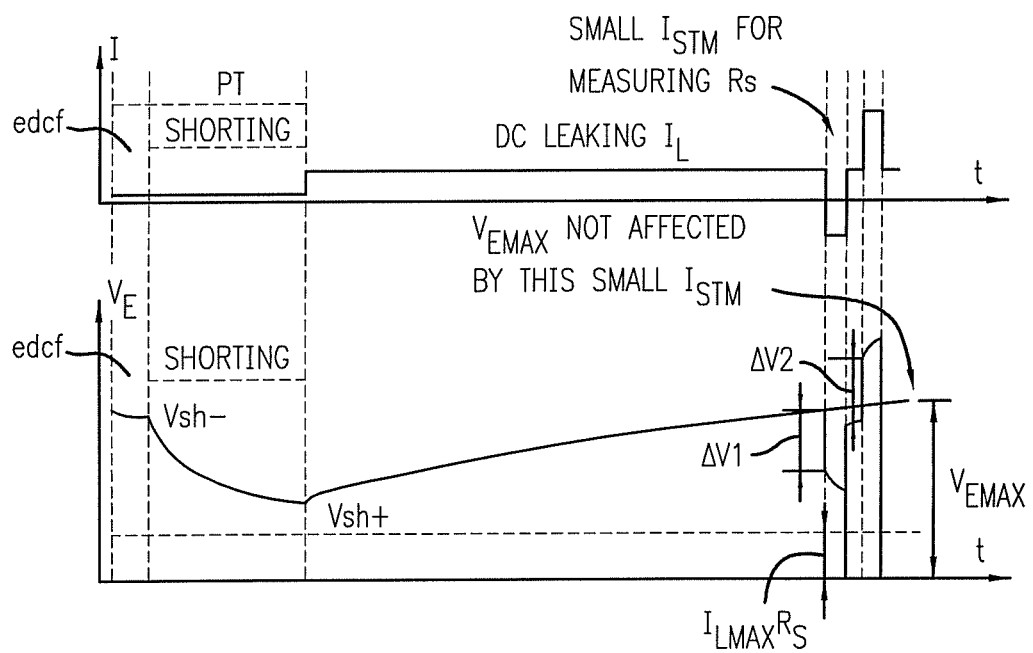
FIG. 13 shows using a small $I_{STIM}$ to measure the $R_S$ and estimate the $V_E$ threshold with a DC leak $I_L$.

FIG. 13 shows that the threshold voltage varies with the electrode impedance, mainly the $R_S$ portion that creates the IR drop when applied $I_{STIM}$ stimulation current. Therefore, both the electrode impedance and its maximum driver output voltage $V_{Emax}$ are needed to be determined in order to determine if the electrode has a sub-EDCF alert.

One method of implementing an efficient sub-EDCF monitoring system based on the algorithm discussed above is illustrated in FIGS. 14A-14C. First, apply a small and narrow biphasic test current pulse to the electrode 1401/1402, wait until it is stabilized 1403, and taking the IR drop measurements 1404-1407. The measured IR drops can be used to calculate the impedance R.sub.S 1408 and V.sub.Emax 1409 values before the shorting to compare against the pre-calculated threshold voltage 1410. From the IR drop measurements one can calculate a pre short maximum voltage and compare that to a threshold leakage voltage value.

Figure 14A:
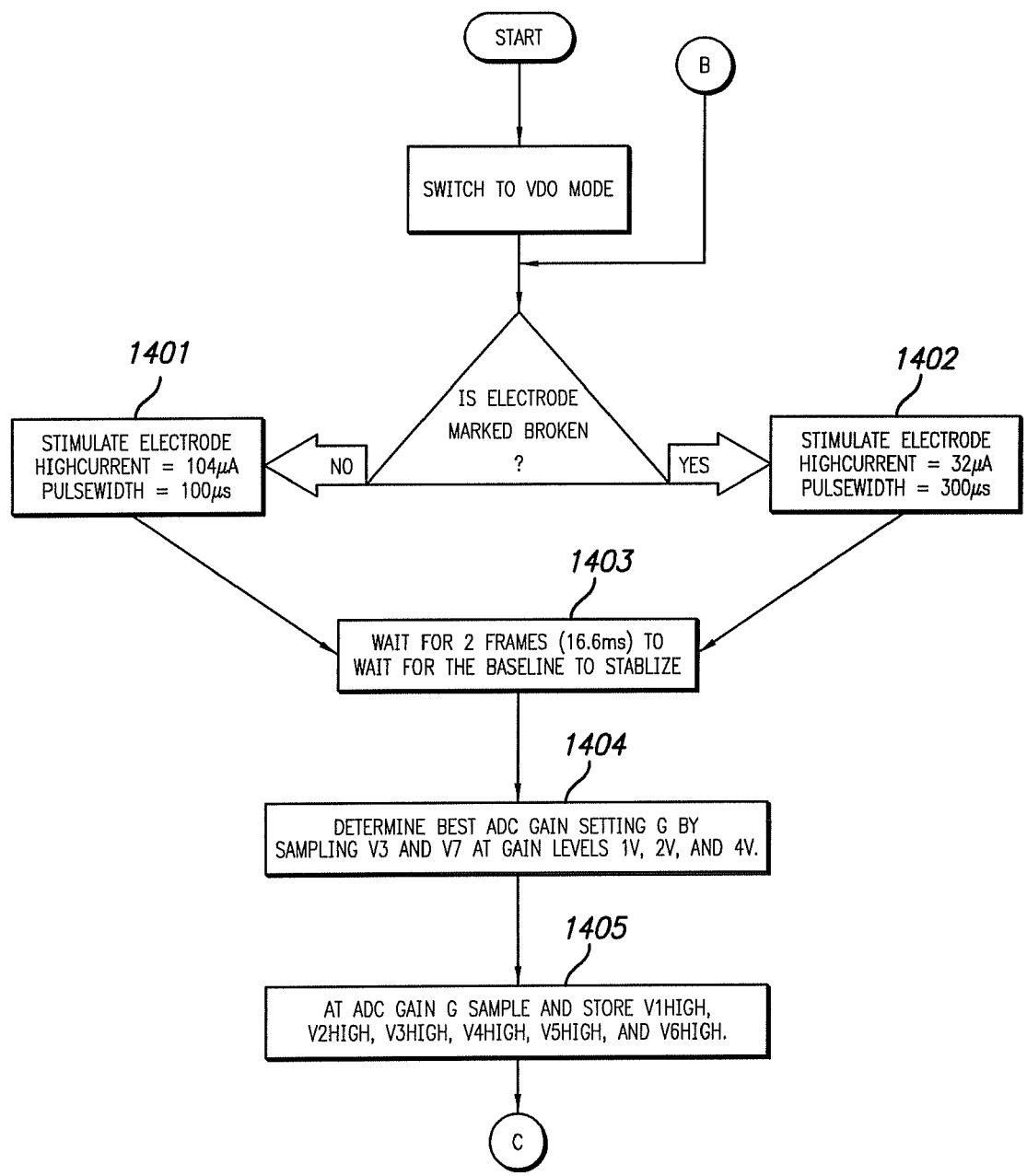
FIGS. 14A-14C show a flowchart for detection via measurement of electrode characteristics.
Figure 14B:
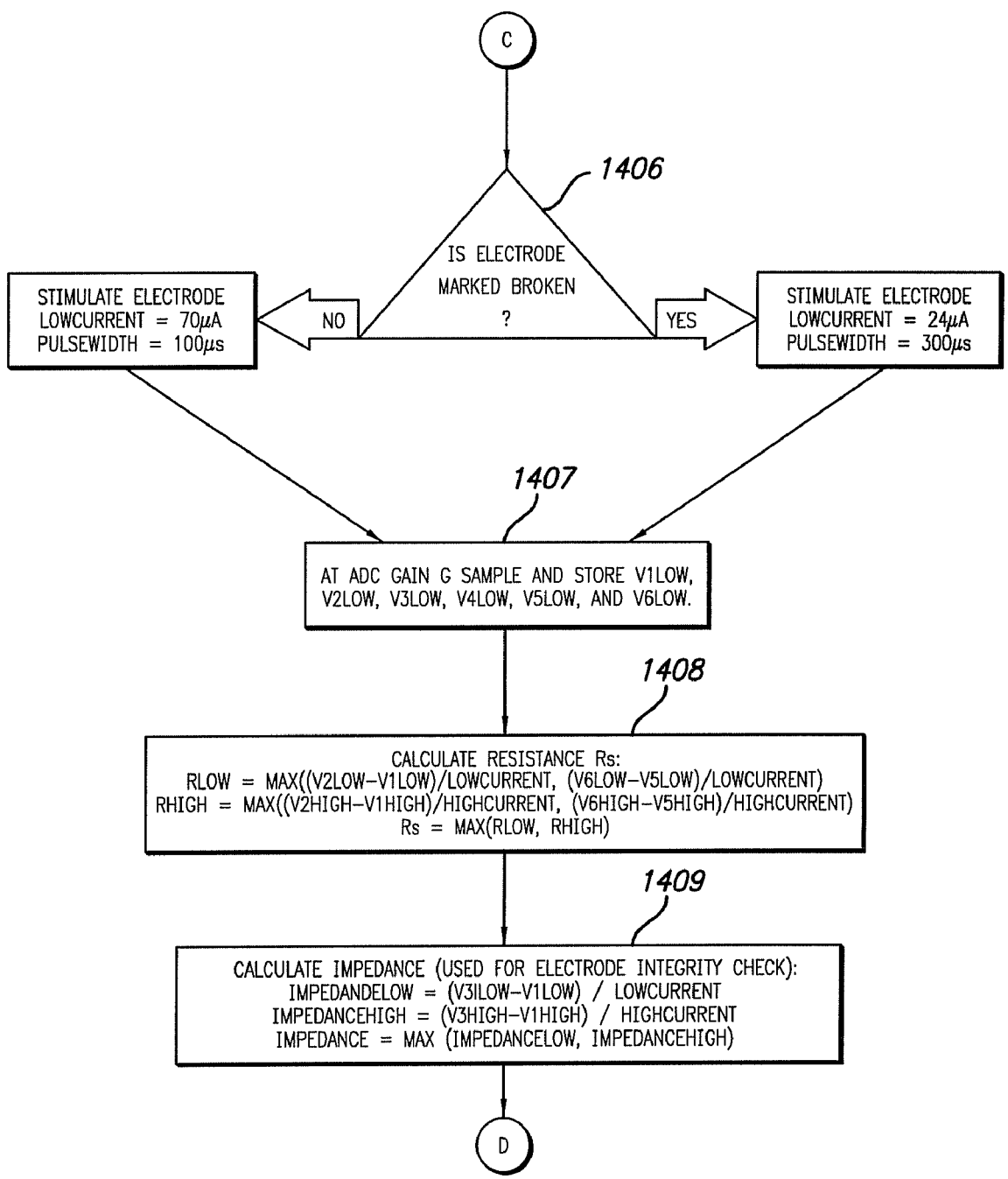
Figure 14C:
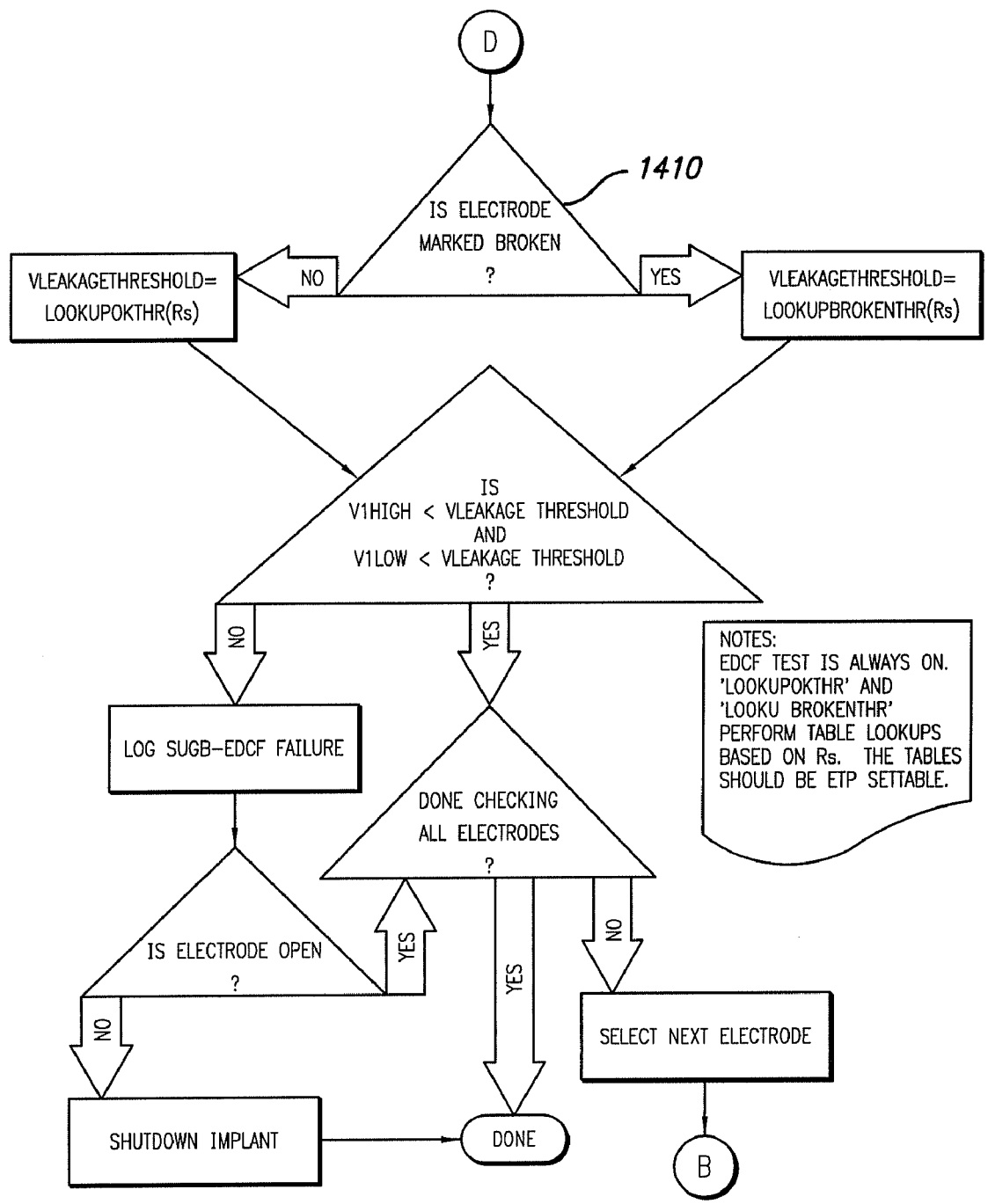

FIG. 15 shows the points where the vision processing unit (VPU) would preferably collect data points V1, V2, V3, V4, V5, and V6 used in the flowchart shown in FIGS. 14A-14C.

Figure 16:
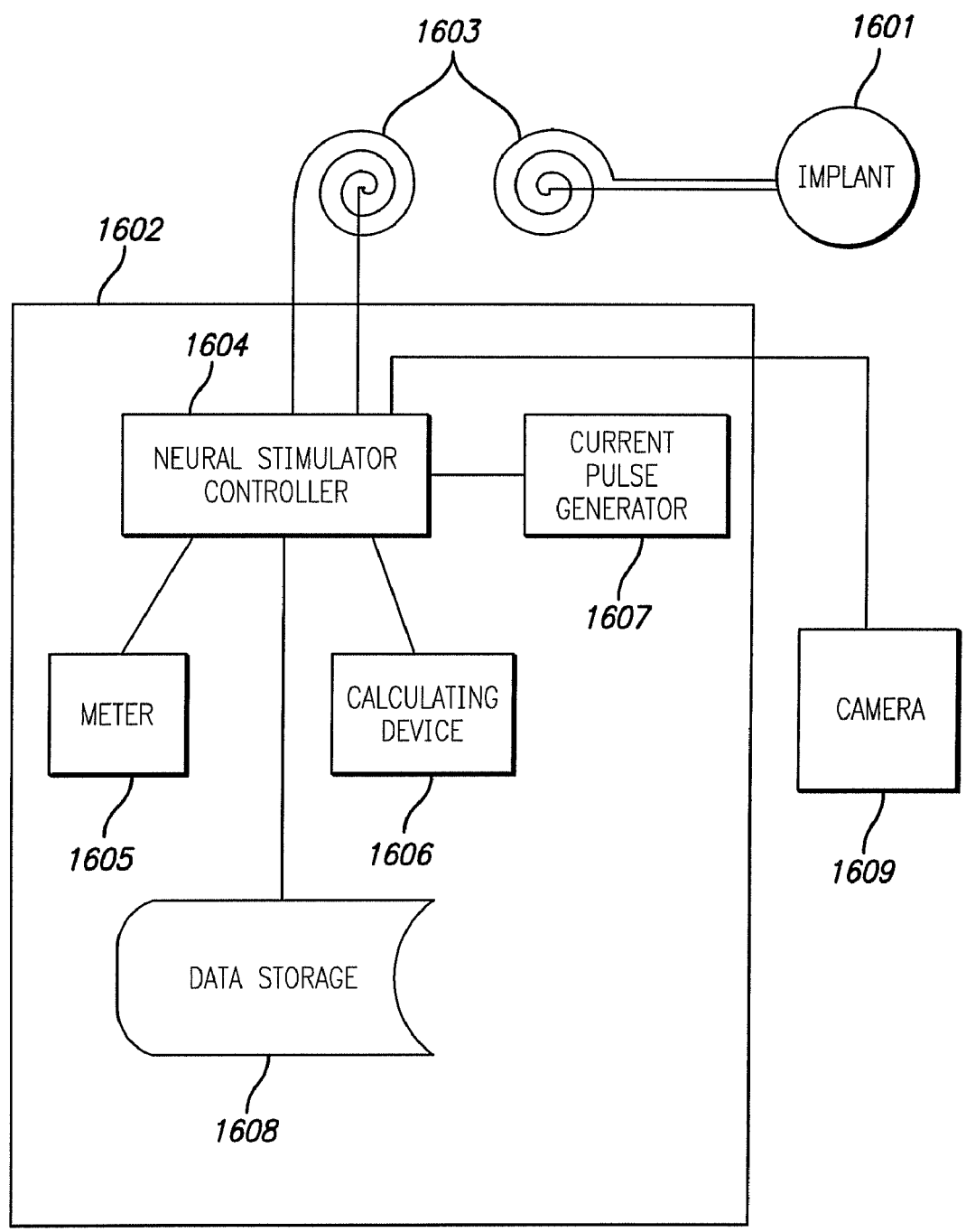
FIG. 16 shows a block diagram of an embodiment incorporating electrode characteristics measurement.

FIG. 16 shows an embodiment of the VPU 1602 and electrode implant 1601. The implant 1601 is connected to the VPU 1602 via inductor coils 1603 and contains at least one electrode connected to tissue. The VPU may comprise a neural stimulation controller 1604, a meter 1605 to take electronics measurements of the electrodes including total power dissipation, a calculating device 1606 to derive values from the measurements including comparing total power dissipation of the neural stimulator to a predetermined maximum tower dissipation, a current pulse generator 1607 to create biphasic current impulses for the electrode tests, and a data storage unit 1608 to record failures and store pre-set values. The meter 1605 may be an RF power control loop or a thermistor. The camera 1609 can be connected to the implant 1601 via the neural stimulation controller 1604, or alternatively can be connected to the implant 1601 via a separate neural stimulation controller (not shown). The meter 1605 can be an inductance meter, a volt meter, a current meter, a waveform monitor, a capacitance meter, or a combination of any of these, depending on which method of electrode testing is required. The VPU can be a single integrated device, or a plurality of devices connected together as shown, in series, with a CPU bus, or in a network.

Accordingly, what has been shown is an improved method and apparatus of stimulating neural tissue for improved response to brightness. While the apparatus and methodology has been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

What is claimed is:

1. A method of controlling the stimulation of neural tissue comprising:
    providing an implantable neural stimulator driving an array of electrodes suitable to stimulate neural tissue;
    generating a test current pulse in said implantable neural stimulator applied to an electrode of said array of electrodes during stimulation of tissue;
    shorting said electrode to ground;
    taking at least one measurement of an IR voltage drop across said electrode during stimulation of tissue;
    calculating a maximum voltage prior to shorting said electrode to ground, from at least one IR voltage drop measurement; and
    comparing said maximum voltage to a predetermined voltage value.

2. The method according to claim 1, further comprising
    determining if said electrode needs to be shut down based on the step of comparing and
    shutting down said electrode if the determining step determines that said electrode needs to be shut down.

3. The method according to claim 1, further comprising
    calculating resistances of said electrode from at least the IR voltage drop measurements and said test current pulse,
    wherein said predetermined voltage value is determined using the resistances of said electrode.

4. The method according to claim 1, wherein the test current pulse are biphasic, comprising an anodic pulse and a cathodic pulse.

5. The method according to claim 4, wherein the test current pulse are configured such that the duration of the anodic pulse is equal to the duration of the cathodic pulse and equal to the duration between the anodic and cathodic pulses.

6. The method according to claim 5, further comprising:
    providing at least one biphasic stimulating current pulse to stimulate neural tissue,
    wherein the test current pulse are of shorter pulse duration and lower maximum current than any biphasic stimulating current pulse.

* * * * *